(12) United States Patent
Euliano, II

(10) Patent No.: US 11,298,485 B2
(45) Date of Patent: Apr. 12, 2022

(54) ESOPHAGEAL PRESSURE CLINICAL DECISION SUPPORT SYSTEM

(71) Applicant: Convergent Engineering, Inc., Newberry, FL (US)

(72) Inventor: Neil Russell Euliano, II, Newberry, FL (US)

(73) Assignee: Convergent Engineering, Inc., Gainesville, FL (US)

(*) Notice: Subject to any disclaimer, the term of this patent is extended or adjusted under 35 U.S.C. 154(b) by 385 days.

(21) Appl. No.: 16/514,270

(22) Filed: Jul. 17, 2019

(65) Prior Publication Data

US 2021/0016035 A1 Jan. 21, 2021

(51) Int. Cl.
*A61M 16/00* (2006.01)
*A61B 5/00* (2006.01)

(52) U.S. Cl.
CPC ......... *A61M 16/024* (2017.08); *A61B 5/0037* (2013.01); *A61M 2205/18* (2013.01); *A61M 2205/3334* (2013.01); *A61M 2205/3344* (2013.01); *A61M 2205/50* (2013.01); *A61M 2205/502* (2013.01);
(Continued)

(58) Field of Classification Search
CPC .............. A61M 16/00; A61M 16/0051; A61M 16/0057; A61M 16/0066; A61M 16/0069; A61M 16/022; A61M 16/024; A61M 16/026; A61M 16/04; A61M 2016/0018; A61M 2016/0027; A61M 2016/0033; A61M 2016/0036; A61M 2205/3331; A61M 2205/3344; A61M 2210/105; A61B 5/037
See application file for complete search history.

(56) References Cited

U.S. PATENT DOCUMENTS

2004/0040560 A1 3/2004 Euliano et al.
2009/0159082 A1 6/2009 Eger
(Continued)

FOREIGN PATENT DOCUMENTS

SE 506521 C2 12/1997

OTHER PUBLICATIONS

Chiumello et al., "The occlusion tests and end-expiratory esophageal pressure: measurements and comparison in controlled and assisted ventilation." Ann. Intensive Care 6, 13 (2016). https://doi.org/10.1186/s13613-016-0112-1.*
(Continued)

*Primary Examiner* — Joseph D. Boecker
(74) *Attorney, Agent, or Firm* — Fleit Intellectual Property Law; Jon Gibbons

(57) ABSTRACT

A novel clinical decision support system (CDS) helps the clinician setup, maintain, and interpret esophageal pressure measurement. The esophageal pressure CDS (Pes CDS) would remind the clinician to do an occlusion test whenever the balloon is first inserted or changes dramatically. It could monitor the occlusion test and provide feedback on the performance and success of the occlusion test. Changes in the patient or monitored data can be tracked by looking for changes in the balloon baseline pressure, changes in the amplitude of the pressure waveform, or changes in the pattern of the Pes waveform. Having information from the ventilator will further increase the ability of the system to determine when Pes is changing unexpectedly.

20 Claims, 18 Drawing Sheets

(52) U.S. Cl.
CPC ........... *A61M 2205/6081* (2013.01); *A61M 2210/105* (2013.01); *A61M 2230/04* (2013.01); *A61M 2230/20* (2013.01); *A61M 2230/30* (2013.01); *A61M 2230/42* (2013.01)

(56) References Cited

U.S. PATENT DOCUMENTS

| | | | |
|---|---|---|---|
| 2015/0217069 A1* | 8/2015 | Novotni | A61M 16/024 128/204.23 |
| 2017/0332943 A1 | 11/2017 | Stenqvist | |
| 2019/0231202 A1* | 8/2019 | Kremeier | A61B 5/085 |
| 2020/0282163 A1* | 9/2020 | Schranz | A61M 16/0051 |
| 2021/0093815 A1* | 4/2021 | Elia | A61M 16/021 |

OTHER PUBLICATIONS

Benditt, Joshua O., Esophageal and Gastric Pressure Measurements published in Respiratory Care, Jan. 2005, vol. 50, No. 1.

Chen, Chang-Wen, et al., Detecting ineffective triggering in the expiratory pphase in mechanically ventilated patients based on airway flow and pressure deflection: Feasibility of useing a computer algorithm, Crit Care Med 2008, vol. 36, No. 2.

Cuvelier, Antoine et al., A Noninvasive Method to Identify Ineffeective Triggering in Patients with Noninvasive Pressure Support Ventilation, Respiration, Clinical Investigations, Published online on Dec. 2, 2009.

Fish, Emily, et al., The Esophageal Pressure-Guided Ventilation 2 (EPVent2) trial protocol: a multicentre, randomised clinical trial of mechanical ventilation guided by transpulmonary pressure. BMJ Open 2014; 4:e006356. doi: 10.1136/omjopen-2014-006356.

Loring, S. H., O'Donnell, C. R., Behazin, N., Malhotra, A., Sarge, T., Ritz, R., . . . Talmor, D. (2010). Esophageal pressures in acute lung injury: do they represent artifact or useful information about transpulmonary pressure, chest wall mechanics, and lung stress?. Journal of applied physiology (Bethesda, Md. : 1985), 108(3), 515-522. doi:10.1152/applphysiol.00835.2009.

Mayaud, Louis & Lejaille, Michèle & Prigent, Hélène & Louis, Bruno & Fauroux, Brigitte & Lofaso, Frédéric. (2014). An opensource software for automatic calculation of respiratory parameters based on esophageal pressure. Respiratory Physiology & Neurobiology, www.elsevier.com/locate/resphysiol.

Talmor, D., Sarge, T., O'Donnell, C. R., Ritz, R., Malhotra, A., Lisbon, A., & Loring, S. H. (2006). Esophageal and transpulmonary pressures in acute respiratory failure. Critical care medicine, 34(5), 1389-1394. doi:10.1097/01.CCM.0000215515.49001.A2.

PCT International Search Report dated Oct. 16, 2020.

PCT Written Opinion of the International Searching dated Oct. 16, 2020.

\* cited by examiner

ESOPHAGEAL PRESSURE CLINICAL DECISION SUPPORT SYSTEM

CROSS-REFERENCE TO RELATED APPLICATIONS

This application is a continuation of U.S. provisional patent application Ser. No. 62/700,016, filed Jul. 18, 2018, the contents of which are incorporated herein in its entirety.

BACKGROUND

The present invention relates to physiologic measurements in the human body, in particular measurements related to breathing. The invention relates to improving and validating measurements useful for ventilating patients and ensuring the lungs and muscles are protected.

Significance of the Esophageal Pressure (Paw) Measurement

This present invention refers to numerous papers which are disclosed in an information disclosure statement filed herewith. To avoid long citations to these papers, these papers are referenced by author's first name and year of publication in parenthesis, e.g., (Talmor 2009) or (Talmor 2014).

The esophageal pressure (Pes) is the pressure in the esophagus, which is a pressure that can be measured and used as a surrogate for other pressures in the body with high clinical implications. Most applications used when measuring Pes are when the patient is receiving mechanical ventilation in a critical care setting. The Pes is a surrogate measure of the pleural pressure (Ppl), the pressure used during spontaneous breathing to expand the lungs and draw in air. The Ppl on the lungs is proportional to the rate of flow and the amount of effort exerted while breathing. The Ppl along with the airway pressure (Paw) can be used to estimate transpulmonary pressure (PL). Depending on the application of the Pes measurement the gastric pressure (Pga) may also be collected allowing for calculation of the transdiaphragmatic pressure (Pdi). According to Talmor et al., (2006) PL is 5 cm $H_2O$ lower than measured Pes, based on a healthy volunteer study group lying in supine position. They also reported that the Pes reading could vary by 2 cm $H_2O$ as a limitation of the equipment. (Talmor 2006) In later research Talmor et al., state that the pleural pressure varies across the entire esophageal region due to the gravitational gradient, but that there is always an 'effective' value that represents the observed lung volume and flow the best. (Talmor 2009) Talmor et al., further describe the relationship between PL and Pes, drawing on the fact that the Ppl affects pressure changes on the lung surface and represents a drive pressure such that the difference between Paw and Pes is a valid estimate of transpulmonary pressure (PL). (Talmor 2014)

The Pes signal has been used to calculate and interpolate information for the respiratory system, in particular the respiratory effort. Measuring the respiratory effort is of particular interest when evaluating the effectiveness of the breaths administered by a ventilator when a patient is receiving mechanical ventilation assisted breaths. Patient-ventilator asynchrony occurs when the patient's breathing efforts are not synchronized with the ventilator's flow delivery. When a patient make an inspiratory effort the Pes signal will change; however during patient-ventilator asynchrony this effort is not detected in the airway pressure and is missed by the ventilator. Thus accurately determining patient-ventilator asynchrony is commonly done with the Pes signal (Chen 2008, Thille 2006, Cuvelier 2010).

Another measure of respiratory effort of great interest to a clinician while caring for a critically ill patient is the patient's work of breathing (WOB). WOB is a measure of how much work is being done for the patient to breathe. Elevated WOB levels will predispose the patient to fatigue; however, inadequately low WOB levels will cause the diaphragm to atrophy. In the respiratory system, work is calculated as the product of pressure times the volume. When using the ventilator pressure (airway pressure) one can calculate total WOB; however it is only the patient's work of breathing that is of interest. Using instead Pes, it is possible to partition the WOB into components and to identify how much work the patient is actually performing. Ventilators and respiratory monitors with built in Pes measurement ports can calculate WOB, often described in joules and normalized work units (J/min and J/L). (Benditt 2005)

The Pes signal has been used to calculate and interpolate information for the respiratory system, in particular differentiating the contributions from the lung and chest wall in the total respiratory system elastance (the inverse of compliance). As with WOB, the elastance has multiple components, and with use of the Pes the lung compliance can be garnered. As Talmor et al., explain, the Open Lung approach measures the pressure difference in both the Paw and the Pes waveforms each with respect to the tidal volume. Chest wall elastance (Ecw) is the change in Pes divided by the tidal volume. Similarly elastance of the total respiratory system (Ers) is the change in Paw divided by the tidal volume and the elastance of the lung (EL) is the change in pleural pressure divided by the tidal volume. Thus Ppl=Paw*(Ecw/Ers). (Talmor 2014)

Benditt et al., also describe a method using an imposed brief breathing pause interrupting flow to the patient from the ventilator to equalize the pressure in the mouth and the alveoli. During the brief pause and at the end of exhalation when flow is zero the pressures at the airway (Paw), esophageal (Pes), and outside atmosphere pressure are all collected. The lung compliance is the CL=VT/((Paw−Pes) end inhalation−(Paw−Pes)end-exhalation), and the chest wall compliance is Ccw=VT/((Pes−Patm) end inhalation−(Pes−Patm) end-exhalation) in which Patm is atmospheric pressure. (Benditt 2005)

The Pes signal has been used to calculate and interpolate information for the respiratory system, in particular estimating the lung pressure to correctly set the positive end expiratory pressure (PEEP) setting on a ventilator. ARDS patients receiving critical care in a hospital setting often have a reduced chest wall compliance, edema, or abdominal distention elevating the Pes. Clinicians often increase PEEP to counteract the effect of ARDS to prevent increased atelectasis. (Talmor 2014) Atelectasis can be identified by evaluating Pes and Paw at end exhalation and end inhalation. (Talmor 2006) Furthermore PEEP can be adjusted according to each patient's lung and chest-wall mechanics. A ventilator strategy using esophageal pressures to estimate the transpulmonary pressure significantly improves oxygenation and compliance. (Talmor 2008) Auto PEEP (excess volume above baseline or PEEP at the end of a breath) is an issue not unique to ARDS patients. Using the Pes signal is the most accurate way to calculate auto-PEEP. The change in Pes from when the patient initiates effort until the flow is moved through the mouth is proportional to the amount of auto-PEEP. (Talmor 2014) Automatic evaluation of Pes has been shown to calculate auto-PEEP. (Mayaud 2014)

Depending on the use of Pes it is common to simultaneously record the gastric pressure (Pga). Measuring both the Pes and the Pga allows one to calculate the extent of the respiratory muscle function. Respiratory muscle function can be measured with the Pes because it has information about the diaphragm embedded in it. The diaphragm is not easily accessible for direct clinical assessment. The pressure across the diaphragm is (Pdi) is the Pga-Pes. (Benditt 2005) Mayaud et al., explained the pressure time product of the diaphragm (PTPdi) can be calculated from the Pdi, narrowing in on the work of only the diaphragm. Specifically, knowing the PTPdi is valuable because it allows for the distinction of flow reversal (a commonly assumed sign of auto-PEEP) to be caused by auto-PEEP or created by external muscle activity. (Mayaud 2014)

The pressure time product (PTP) can be calculated with use of both the Pes and Pga signals. The pressure-time product is calculated as the product of the time spent in muscle contraction during inspiration as a percent of the total respiratory cycle time and the pressure generated by the muscle during inspiratory contraction. (Benditt 2005)

The Pes signal has also been used to calculate and interpolate information for the cardiovascular system and the digestive system. Due to the proximity of the esophagus to the heart the Pes signal can be used to determine cardiovascular information, in particular the left atrium distending pressure. Changes in heart pressure are informative for cardiovascular reasons, but the application of positive pressure ventilation with mechanical ventilators impacts the cardiovascular system. Talmor et al., explain that the large negative swings in Pes that occur during difficult weaning account for the increases in venous return into the pulmonary circulation and in left ventricular afterload caused by the increased transmural intrathoracic pressures. (Talmor 2014)

Methods in Measuring Esophageal Pressure (Pes)

The common method of measuring the esophageal pressure (Pes) is through a balloon catheter or with a solid state pressure sensor. The benefit of using the balloon catheter is that it is inexpensive and can be disposable (single use). Benditt et al., (2005) describe the use of the esophageal balloon, "the device consists of a thin polyethylene catheter with multiple small holes in the distal 5-7 cm of its length. The distal end of the catheter is then placed in a 10-cm latex balloon that prevents the holes in the catheter from being occluded by esophageal tissue and maintains a column of air within and around the catheter, in order to measure pressure in the surrounding structure. The proximal end of the catheter is attached to the pressure transducers and recording equipment. The balloon catheter (or catheters) is passed through the nares into the posterior pharynx. At this point the subject is instructed to swallow (if spontaneously breathing) and the catheter is passed into the esophagus and then into the stomach. The catheter is attached to the transducer/recorder system, and 2.0 mL of air is injected into the balloon. Then 1.5 mL of air is withdrawn, to leave 0.5 mL of air in the system to partially inflate the balloon and the catheter. The presence of a positive pressure deflection during inspiration indicates that the balloon is located in the stomach, if the diaphragm is functioning. The catheter is then slowly withdrawn into the esophagus, where the pressure reads negative during inspiration. The catheter is then withdrawn another 10 cm after the initial negative deflection, to ensure that the entire catheter is within the esophagus. The catheter will be posterior to the heart, and cardiac pulsations appear on the waveform. The catheter tip will be approximately 35-45 cm from the nares. It is helpful to mark the catheter at 10-cm intervals prior to placement, and some commercially made devices are pre-measured and marked. If a gastric balloon is being placed, the same procedure is followed, but the catheter is not withdrawn and 2.0 mL of air is added to the system. If diaphragm paralysis is present, the gastric pressure may not be positive during inspiration and so the gastric catheter tip will have to be placed beyond the point where cardiac pulsations are seen, or at least to 45 cm from the nares."

Talmor et al., describe an occlusion test which is performed to validate the correct placement of the esophageal balloon. "In a spontaneously breathing patient, the classic method to validate the Pes measurement is the dynamic occlusion test. It consists of measuring the ratio of change in esophageal pressure to the change in airway opening pressure ($\Delta Pes/\Delta Paw$ ratio) during three to five spontaneous respiratory efforts against a closed airway. A $\Delta Pes/\Delta Paw$ ratio close to unity indicates that the balloon provides a valid measure of Ppl changes. This test does not require patient cooperation. The occlusion test has been validated in normal adults and pediatric patients; it has also been applied in paralyzed subjects. In sedated and paralyzed patients, the occlusion test is performed by applying manual compression on the chest during airway occlusion. Factors influencing the $\Delta Pes/\Delta Paw$ ratio during the occlusion test include the position of the balloon, the amount of air injected into the balloon, the patient's position, and lung volume. These factors should be checked periodically to ensure the best concordance between swings in Pes and in Paw during the occlusion test. The acceptable range of $\Delta Pes/\Delta Paw$ ratio during the occlusion test is 10-20% (i.e., from 0.8 to 1.2). Cardiac contractions can distort the Pes signal. Patient position, balloon position, and lung volume may influence the amplitude of Pes changes due to the cardiac artifact. Esophageal contraction due to peristalsis is sometimes present and is easily detected (as a large increase in pressure that bears no relationship with respiratory cycles): in this case, Pes measurement should be interrupted until Pes returns to its baseline value. (Talmor 2014)

Problems While Using Pes in a Clinical Setting

Unfortunately, using an esophageal balloon can be difficult for the average healthcare practitioner. Problems using the balloon include: over inflation of the balloon, under inflation of the balloon, incorrect placement of the balloon (too high or too low), leaks in the balloon that slowly deflate the balloon. Incorrect placement or inappropriate inflation may yield deceptive or meaningless data.

As described above, a well-known technique to determine if the balloon is placed, inflated, and working properly is the occlusion test. The occlusion test involves blocking the patient airway during a patient inspiratory effort. Because there is no gas flow in or out of the lung, the pressure in the chest equalizes throughout and provides an ability to match the pressures at the patient airway with the pressure in the lungs and esophagus. Since clinicians do not have the tools to validate an occlusion test some clinicians drop the esophageal balloon and do no not do an occlusion test, trusting their judgement on whether the esophageal pressure tracing looks correct. Some clinicians do the occlusion test, but "eyeball" the pressure drops without actually calculating the actual pressure drop.

SUMMARY

There are many advantages to using esophageal pressure monitoring for patients, but the sensors are difficult to place and difficult to maintain accurate readings. A clinical decision support system (CDS) that can help the clinician setup, maintain, and interpret the esophageal pressure measurement would be useful. The esophageal pressure CDS (Pes CDS) would remind the clinician to do an occlusion test whenever the balloon is first inserted or changes dramatically. It could monitor the occlusion test and provide feedback on the performance and success of the occlusion test. Changes in the patient or monitored data can be tracked by looking for changes in the balloon baseline pressure, changes in the amplitude of the pressure waveform, or changes in the pattern of the Pes waveform. Having information from the ventilator will further increase the ability of the system to determine when Pes is changing unexpectedly. If the ventilator settings change, the Pes waveform is likely to change as well due to changing demands on the patient. If no ventilator settings change, a Pes waveform change is more likely due to a change in the pressure sensor that may need attention. In addition, a model of the physiology of the patient and/or the esophageal sensor, ventilator, and the airway sensor can be created that will help track different variables and provide additional information regarding whether the patient, ventilator, or esophageal sensor are responsible for any measured changes.

More specifically, the present invention is a method, computer program product and a system to improve the operation of a ventilator. The system includes one or more sensors to provide measurement data for each of esophageal pressure data, airway pressure data, and airway flow data from a patient being ventilated. The processor is electronically coupled to the sensors and receives the measurement data therefrom, the processor compares the esophageal pressure data with changes to one or more of airway pressure data and air flow data to determine an accuracy or clinical reliability of the esophageal pressure data.

In one example the accuracy or reliability of the esophageal pressure data is determined using a computer processor by comparing the airway pressure data to the esophageal pressure data during one or more of a trigger portion of a breath, an end exhalation portion of a breath, or an end expiratory pause of a breath from the patient being ventilated. This comparing may occur over multiple breaths from the patient being ventilated and the processor further determines a trend that is included in the accuracy of the esophageal pressure data. In order to assist with determining the accuracy of the esophageal pressure data, the system may suggests or automatically make changes to ventilator to extend a trigger time or to impose an end expiratory pause, or both to determine the accuracy of the esophageal pressure data.

A model may be used that determines the accuracy of the esophageal pressure data. In this example the model uses as inputs one or more of airway pressure data, flow data, from the measurement data and the model compares predicted esophageal pressure data to the measured esophageal pressure data.

In another example the computer processor uses esophageal pressure data to determine an intrinsic PEEP in the patient. The intrinsic PEEP may be automatically detected by measuring a change in esophageal pressure data during a patient triggering before a change to one or more of the airway pressure data and the airway flow data at a start of a breath of the patient. Further, the computer processor may use settings from a ventilator control algorithm as input along with a degree of the intrinsic PEEP to automatically calculate changes to settings in the ventilator. The settings may include one or more of a PEEP setting, a sensitivity level, a cycling criteria, a pressure support level, a tidal volume, a breath rate, and an inspiration-expiration (I:E) ratio.

In another example, the computer processor uses a transpulmonary pressure data to calculate a change in a PEEP. The PEEP is managed by maintaining the transpulmonary pressure data at end of exhalation of the patient in a predetermined range. The transpulmonary pressure data is used by the processor to calculate a change in a tidal volume of the patient to maintain peak transpulmonary pressure below a predetermined level.

In another example the computer processor automatically makes changes to a ventilator control algorithm when the accuracy of the esophageal pressure data is above a threshold of accuracy. The computer processor may automatically make changes to a ventilator control algorithm including using esophageal pressure data to control breath delivery.

The system may include a display which indicates a status of the patient or system using the esophageal pressure data. This status may be used as part of a clinical decision support (CDS) to improve the use of the ventilator. In another example the display is used to improve a placement and setup of the one or more sensors to provide the esophageal pressure data. Also, the display may provide a status on whether an occlusion test is successful from an analysis of a change in esophageal pressure divided by the change in airway pressure during times of zero flow. The esophageal pressure data, the airway flow data and the airway flow data to indicate a direction to relocate the one or more sensors in the esophagus of the patient. The status on the display may be one or more of a warning, a status indicator, a color coding of an esophageal waveform, and a parameters derived from the esophageal waveform.

In another example processor in the system uses esophageal pressure data to estimate patient-ventilator asynchrony. A degree of patient-ventilator asynchrony is calculated as an asynchrony index (AI) and the AI is displayed on the display. The degree of patient-ventilator asynchrony includes determination of different types of asynchrony including one or more of missed triggers, double triggers, autotriggers, cycling delay, and premature cycling. Moreover, the degree of patient ventilator asynchrony and one or more of a PEEP setting, a sensitivity level, a cycling criteria, a pressure support level, a tidal volume, and a breath rate are used to improve patient ventilator asynchrony.

In still another example, a device to measure cardiac data from one or more of ECG and pulse-oximetry is included with the system. The processor is electronically coupled to the devices to measure cardiac data. The processor uses the cardiac data to reduce artifacts from at least one of the esophageal pressure data, airway pressure data, and airway flow data caused by cardiac influence on the one or more sensors. The cardiac data and the airway pressure data or the airway flow data is input into a model to reduce an influence from the cardiac data on one or more waveforms from the sensors. The model may be an adaptive filter.

Further, the influence from the cardiac data is extracted to provide information to a clinician about a cardiac system and its influence on a respiratory system. A ventilator control algorithm may use one or more of the esophageal pressure data, the airway pressure data, and the airway flow data with the reduced artifacts as inputs. The ventilator control algorithm is one or more of a pressure regulation algorithm for pressure support ventilation, a breath triggering algorithm, a breath cycling algorithm, a PEEP algorithm, and an algorithm to improve patient-ventilator asynchrony.

BRIEF DESCRIPTION OF THE SEVERAL VIEWS OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Overview of Human Lungs and Thorax

Figure 1:
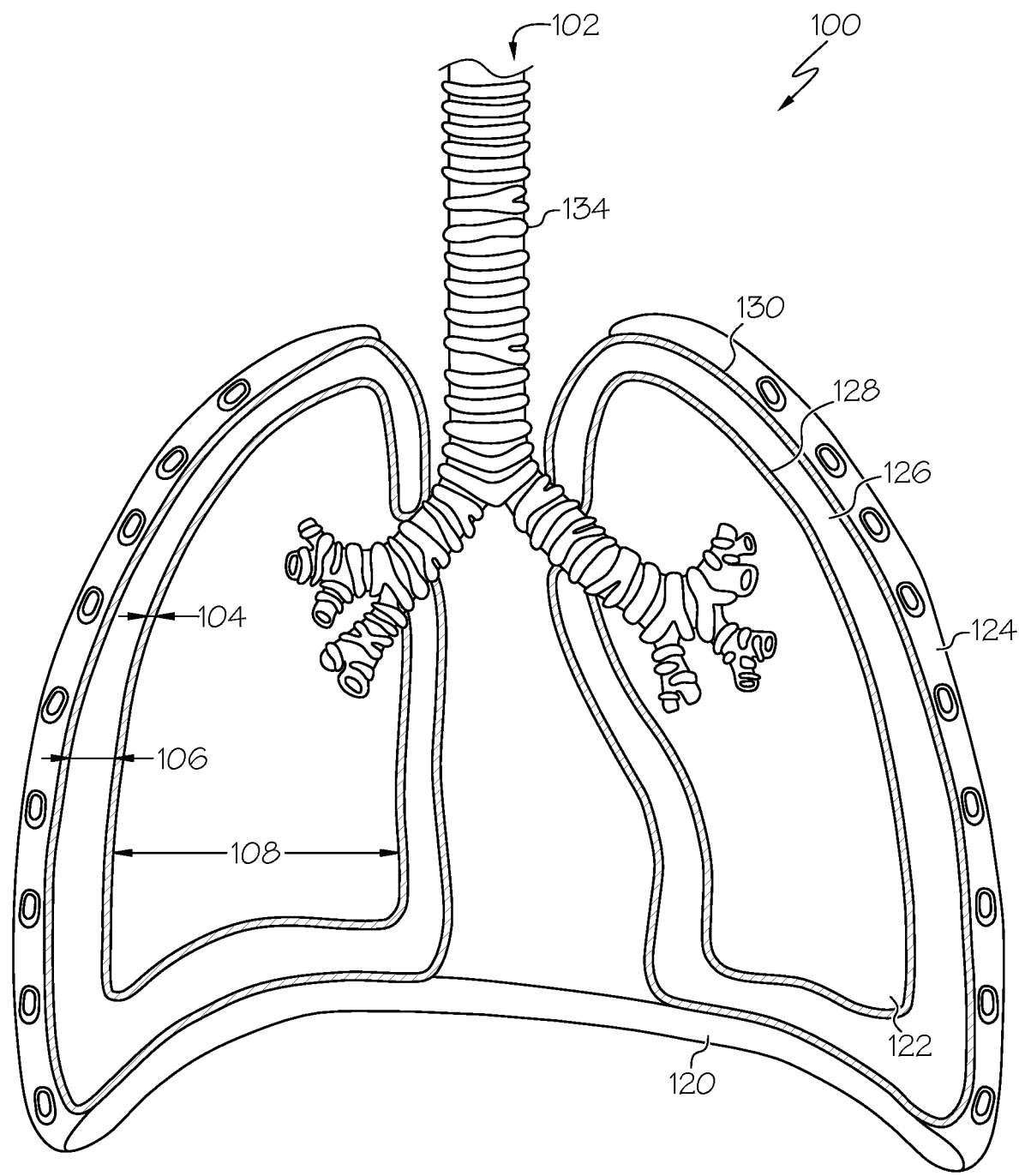
FIG. 1 is a drawing of the major portions of lungs with names of various pressures.

FIG. 1 is a diagram of the lungs 100 and the various pressures of interest during spontaneous breathing without a ventilator, including transpulmonary pressure (PL), intrapleural pressure (Ppl), and intra-alveolar pressure. The pressures shown are atmospheric pressure 102, transpumonary pressure (PL) 104, usually approximately 4 mm Hg, intrapleural pressure (Ppl) 106, typically approximately −4 mmHg and intra-alveolar pressure 108 typically approximately 0 mm Hg.

FIG. 1 also shows major portions of the lungs 100 starting with diaphragm 120, a lung 122, the thoracic wall 124, the pleural cavity 126, the visceral pleura 128, the parietal pleura 130 and the trachea 134.

Figure 2A:
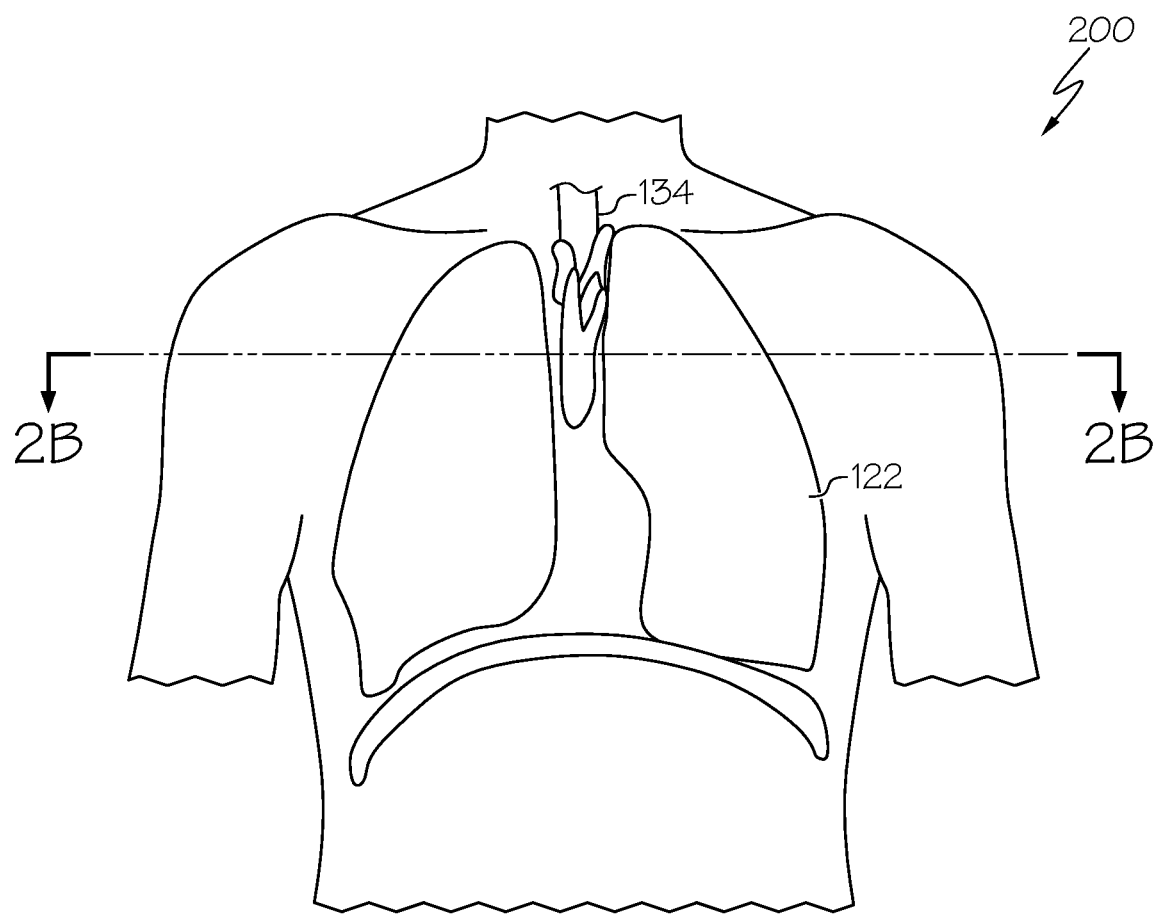
FIG. 2A is an illustration of a human thorax.
Figure 2B:
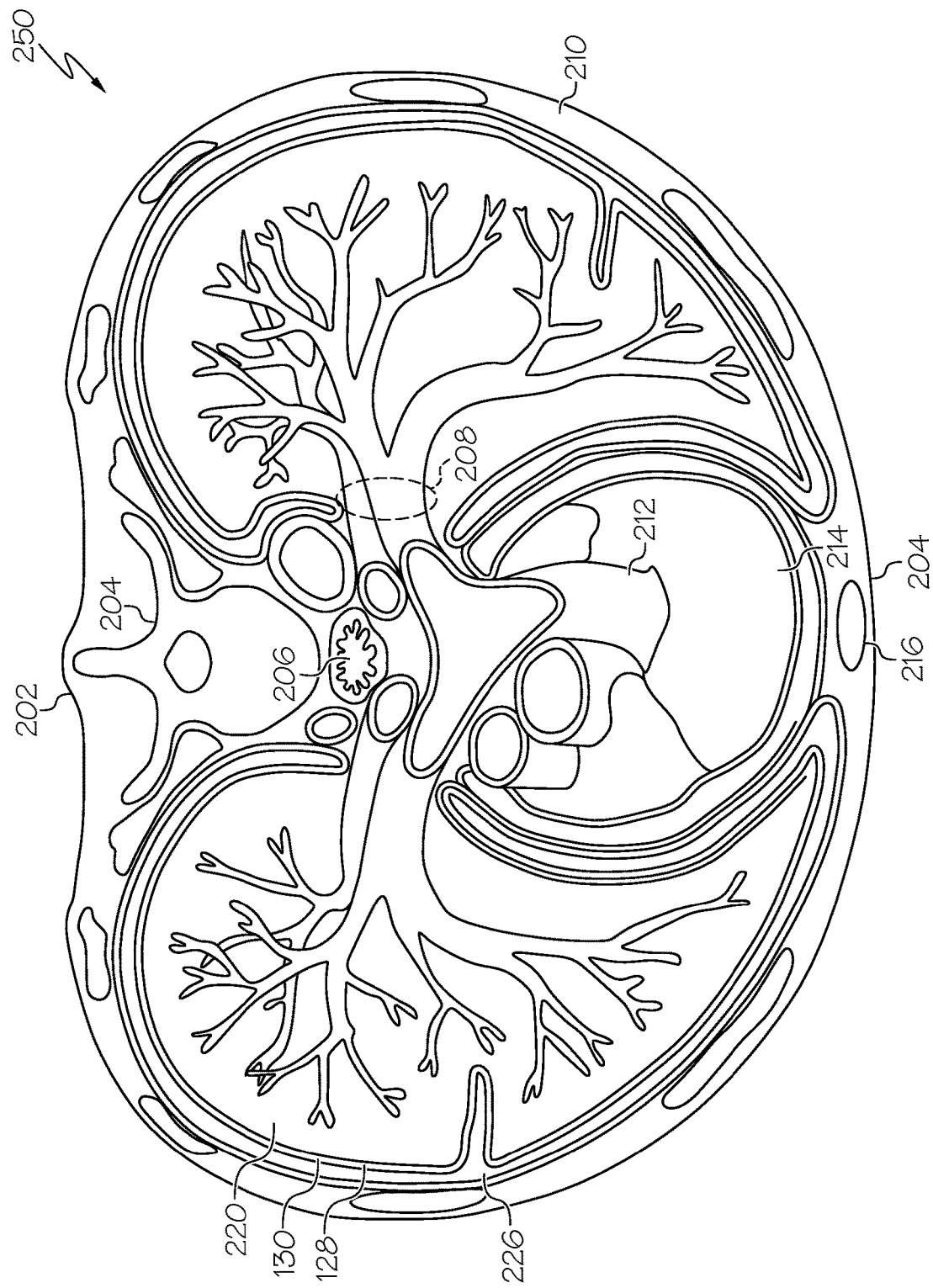
FIG. 2B is a sectional view of the human thorax taken along line 2B to 2B to illustrate the physiology of the lung.

FIG. 2A is an illustration of a human thorax 200 and FIG. 2B is a sectional view of the human thorax 250 taken along line 2B to 2B to illustrate the physiology of the lung. Starting at the top of FIG. 2B is the posterior part of human thorax 202, the vertebra 204, the esophagus 206, the bottom of the trachea forming the root of lung 208, the thoracic wall 210, the pulmonary trunk 212, the heart 214, the sternum 216 and the anterior part of human thorax 218. Also shown is a lung 220, the visceral pleura 128, the parietal pleura 130 and the pleura cavity 226.

Overview of Human Esophagus

Figure 3B:
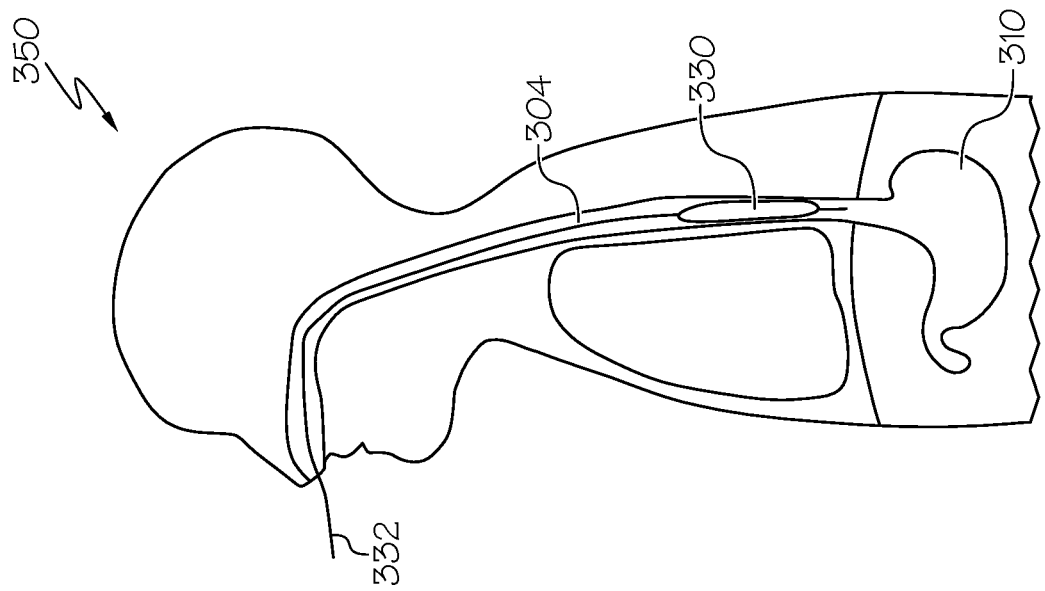
FIG. 3B is a drawing of a human esophagus and stomach with an esophageal balloon and its location relative to the stomach.
Figure 3A:
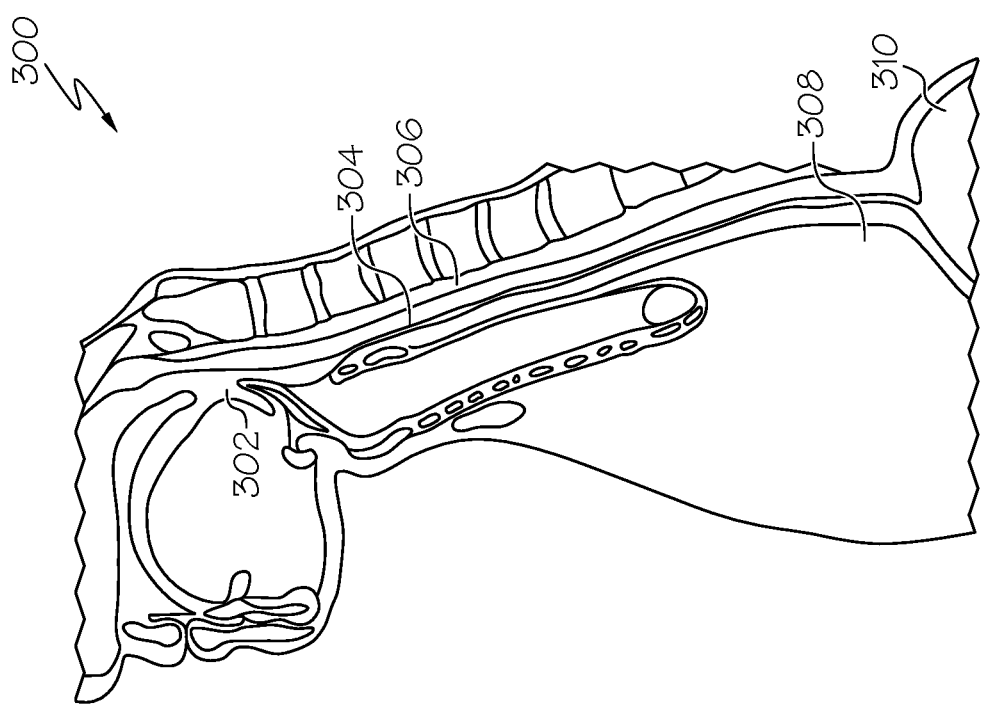
FIG. 3A is a drawing of a human esophagus and stomach.

FIG. 3A is a drawing 300 of a human esophagus and stomach. Shown are the pharynx 302, upper esophageal sphincter 304, the esophagus 306, the lung 308, and stomach 310.

FIG. 3B is a drawing 350 of a human esophagus and stomach with an esophageal balloon. Shown is an esophageal balloon 330 with an inflation tube 332 and its location relative to the stomach 310 in an esophagus 304.

Tool to Support an Occlusion Test

Figure 4:
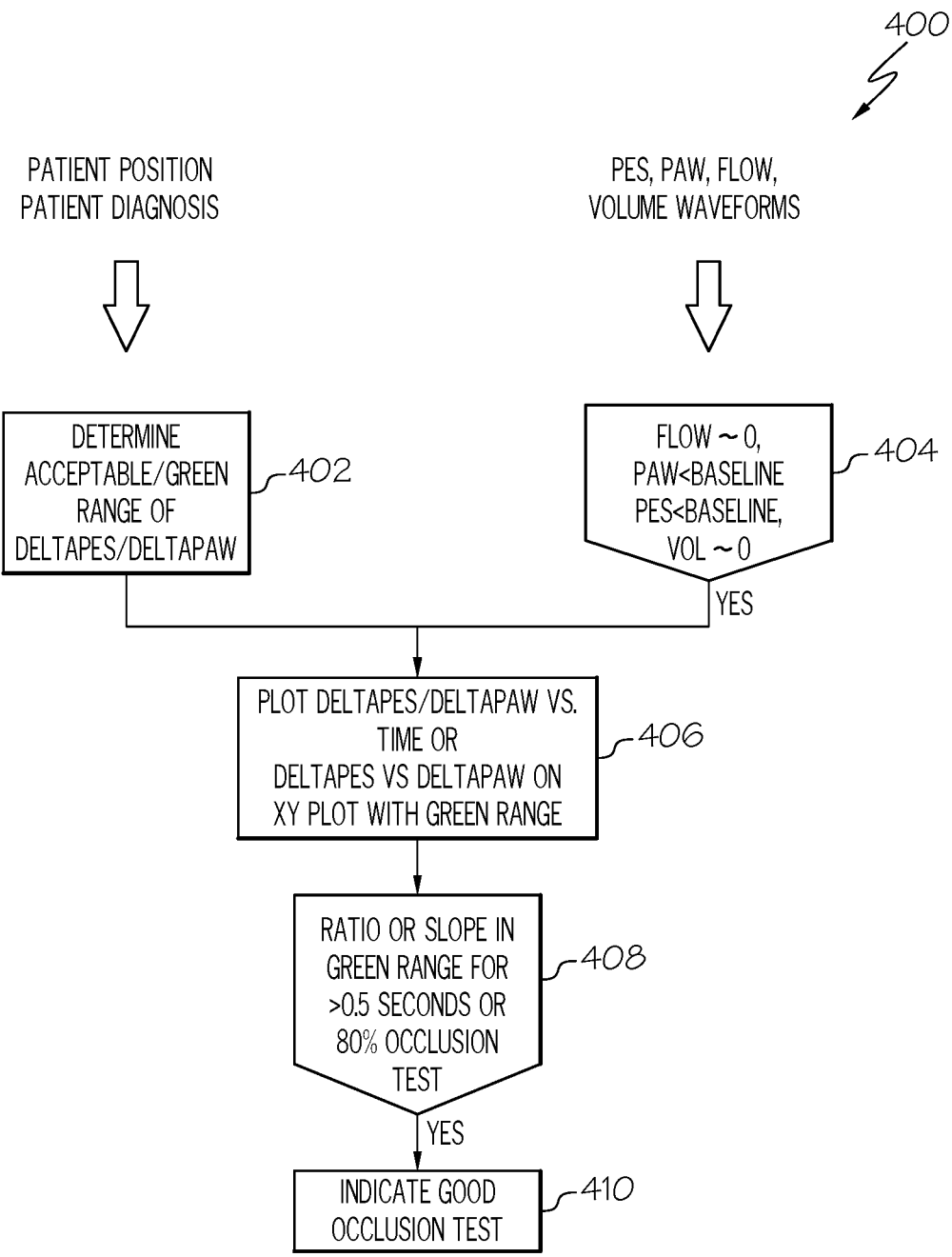
FIG. 4 is block diagram of tool to support the occlusion test.

FIG. 4 is block diagram 400 of tool to support the occlusion test. Using patient position and diagnosis and clinical evidence/experience, an acceptable range of deltaPes/deltaPaw is determined. Normally, this ratio is in the range is 0.8 to 1.2, but can be different with different diseases and patient position/orientation in step 402. When activated in step 404, the occlusion test tool checks the waveforms continuously for locations where the flow is approximately 0 and the Paw (airway pressure) and Pes (esophageal pressure) are falling below baseline, indicating a spontaneous effort (or above baseline if the patient is not spontaneously breathing) with the airway occluded. In one embodiment, the system will also check that the volume is low or close to zero to ensure that the effort occurred when the patient's lung was mostly empty, which produces a better occlusion test. Next in 406, the deltaPes/deltaPaw values are plotted or displayed with a range of acceptable values showed. This can be an x-y plot, a bar that moves up and down towards the desired height, or a number that changes color as it moves towards the correct value. In step 408, when the ratio or slope is maintained for a sufficient amount of time or sufficient fraction of the occlusion test (the time when the Paw and Pes are below baseline and the flow is zero), then the occlusion test was successful, and in step 410 and an indicator can be shown. Sometimes, the process is repeated to ensure the esophageal pressure sensor is working correctly. Graphics and plots provide important feedback to the clinician, but are not necessary to implement the key function of determining when the esophageal balloon is working correctly.

Tool Esophageal Sensor Decision Support System

Figure 5:
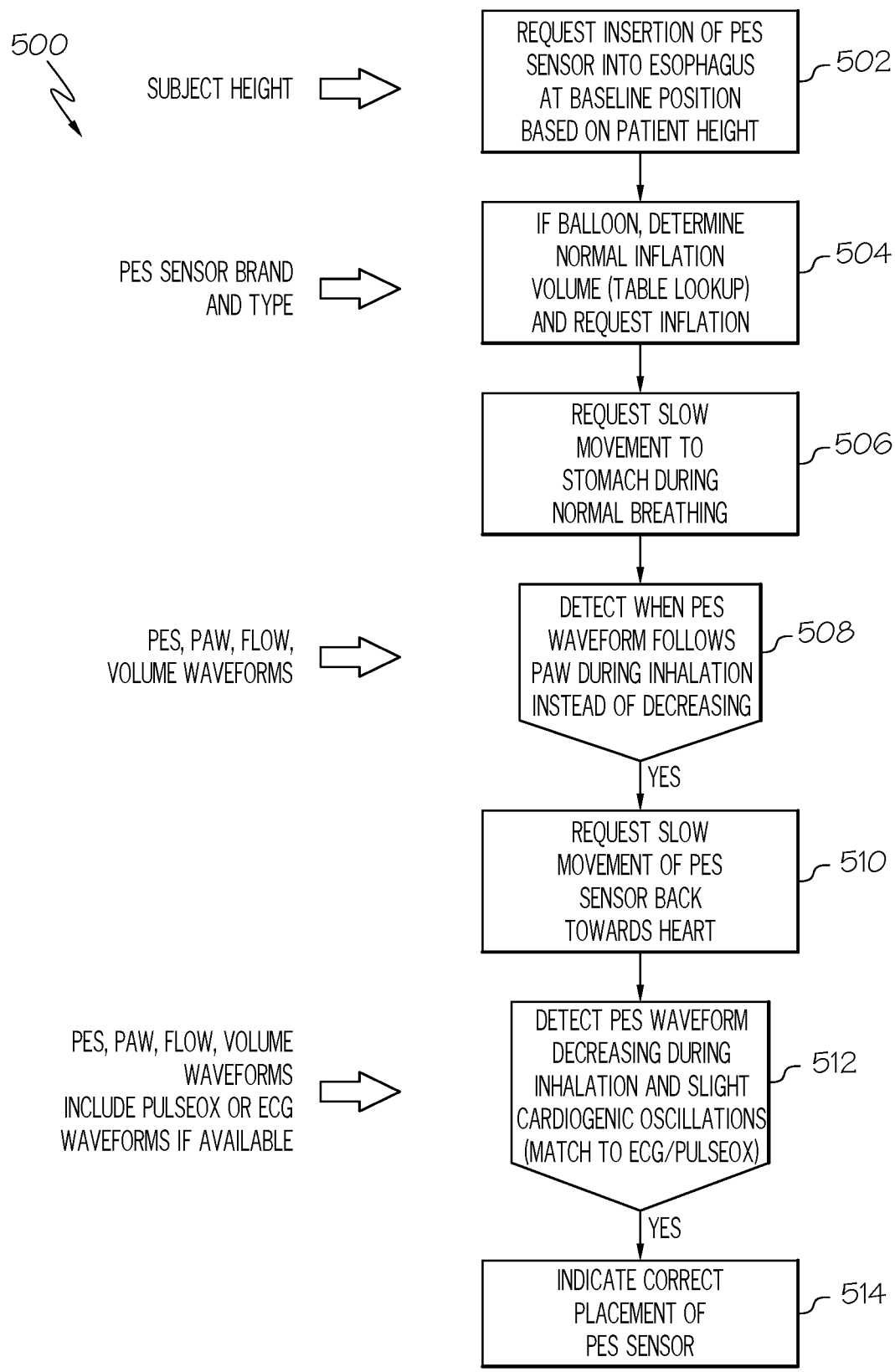
FIG. 5 is the esophageal sensor decision support system can walk the clinician through the process of correctly placing the Pes sensor.

FIG. 5 is an esophageal sensor decision support system 500 that guides the clinician through the process of correctly placing the Pes sensor. In step 502, based on clinical best practices or the subject's height and a formula or table lookup, the clinician is first instructed to place the Pes sensor at a prescribed depth (varies with oral or nasal placement) to start. Next in step 504, if the Pes sensor is a balloon, the system will either automatically inflate the balloon or request the balloon be inflated. The amount of inflation will vary with the type of the Pes balloon being used and can be looked up in a table or with a formula. Next in step 506, the clinician will be asked to move the sensor slowly towards the stomach during normal breathing until the system detects that the Pes waveform reflects that the balloon is in the stomach (e.g. rising Pes during spontaneous inhalation instead of falling) in step 508. Once this occurs, in step 510 the clinician will be requested to slowly pull the balloon back towards the heart for a certain distance (from table lookup) or until small cardiogenic oscillations are seen. In step 512, these oscillations may be validated to be cardiogenic with an optional PulseOx or ECG waveform (e.g., if the frequency or pattern matches the heart rate or waveforms). At this point in step 514, the Pes sensor is in the correct position. Next, the occlusion test should be done to validate the correct inflation (if necessary) and location of the sensor.

Continuous Validation that Pes Sensor is Working Correctly

Figure 6:
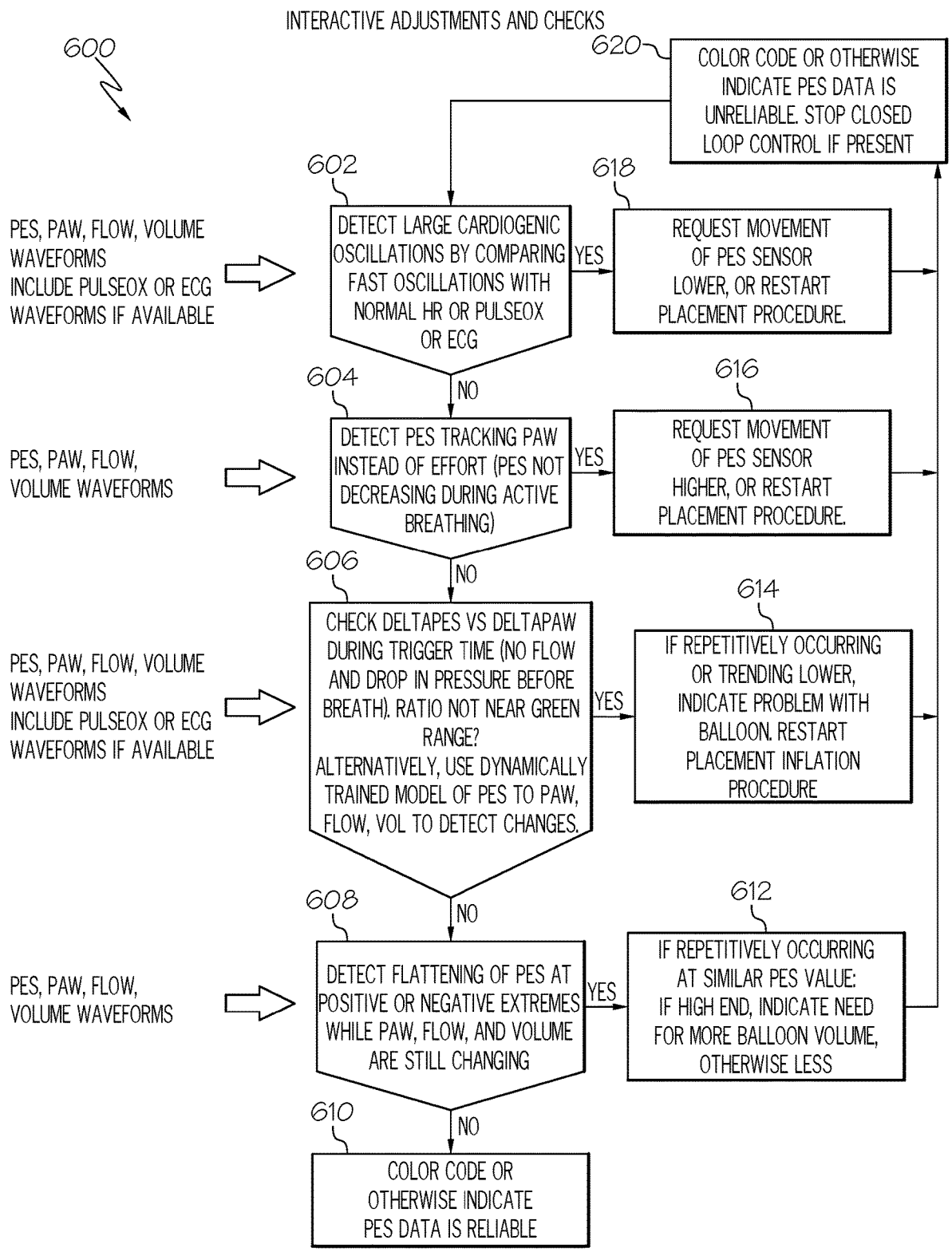
FIG. 6 is a flow diagram of continuously using Pes and Paw to constantly validate that the Pes sensor is working correctly.

FIG. 6 is a flow diagram 600 of continuously using Pes and Paw to constantly validate that the Pes sensor is working correctly. This algorithm describes example methods of monitoring the Pes sensor for validity over time as the patient is being ventilated. For example, if cardiogenic oscillations become large or are trending upward, it may indicate that the sensor has moved upwards toward the heart and should be moved lower (or redo the placement procedure). If the Pes signal starts moving in the opposite direction (higher instead of lower) during inhalation, the sensor has likely moved to the stomach and should be pulled back towards the heart until the condition is fixed (or restart the placement procedure). The time between start of effort and start of ventilator flow (patient effort but no flow) is similar to a mini occlusion test. Measuring deltaPes and deltaPaw at this time will provide data that can be used to indicate that the Pes sensor is still working, is trending towards not working, or is working poorly. Another method of validating the validity of the Pes waveform is to create a model relating the Paw, Flow, and Volume waveforms to the Pes waveform. If this model changes dramatically over time, the Pes waveform may be no longer valid. Similarly, if the Pes waveform is flattening at high or low Pes values, the volume in the balloon is probably incorrect and should be adjusted.

In all the cases where the Pes sensor values are "in doubt", the Pes values can be color coded differently or an indicator can be used to indicate to the clinicians that the Pes sensor may not be reporting valid data.

More specifically the flow diagram 600 starts in step 602 with detecting large cardiogenic oscillations by comparing fast oscillations with normal heartrate (HR) or Pulse oximetry (PulseOx) or ECG (electrocardiogram). In the event that large cardiogenic oscillations exist, the process proceeds to step 618 to request movement of Pes sensor lower, or restart placement procedure. The process continues to step 620 in which color code or otherwise indicate Pes data is unreliable. The closed loop control, if present, is stopped. The process loops back to step 602. On the other hand, in the event that large cardiogenic oscillations are not detected, the process continues to step 604.

In step 604 the process detects if Pes is tracking Paw instead of effort (Pes not decreasing during active breathing). In the event that Pes is tracking Paw instead the process proceeds to step 616 to request movement of Pes sensor higher, or restart placement procedure. The process continues to step 620 in which color code or otherwise indicate Pes data is unreliable. The closed loop control, if present, is stopped. The process loops back to step 602. On the other hand, in the event that Pes is not tracking Paw, the process continues to step 606.

In step 606 the process checks whether the deltaPes versus deltaPaw ratio during trigger time is not near the green or predetermined acceptable range. The trigger time is the time at which there is no flow and a drop in pressure before breath. In another example, the process uses dynamically trained model of Pes from Paw, flow, and/or volume to detect changes. In still another embodiment the process uses more than one. In the event that check is not in an acceptable range the process proceeds to step 614 to determine if this is repetitively occurring or trending lower, which indicates a problem with the balloon and to restart placement inflation procedure. The process continues to step 620 in which color code or otherwise indicate Pes data is unreliable. The closed loop control, if present, is stopped. The process loops back to step 602. On the other hand, in the event that check is in an acceptable range, the process continues to step 608.

In step 608 the process detects the flattening of Pes at positive or negative extremes while the Paw, flow, and volume are still changing. In the event that Pes is flattening the process proceeds to step 612 to determine if this process is repetitively occurring at similar Pes values. if the flattening is occurring at a high pressure, the system indicates need for more balloon volume, otherwise less balloon volume. The process continues to step 620 in which color code or otherwise indicate Pes data is unreliable. The closed loop control, if present, is stopped. The process loops back to step 602. On the other hand, in the event that the Pes is not flattening, the process continues to step 610.

In step 610 an indication such as color on a display or audio alert or other indicator is used to indicate that the Pes data is reliable i.e. meets a settable threshold for accuracy.

Example Display Screens

Figure 7A:
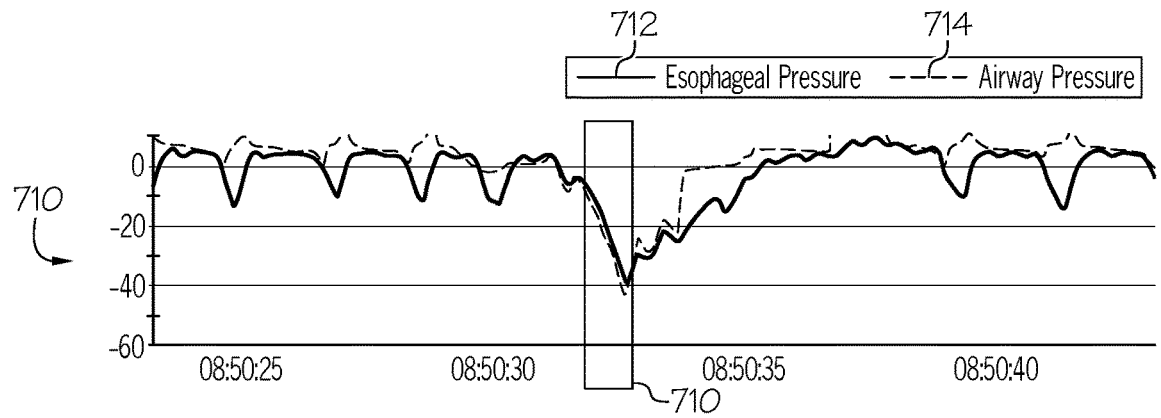
FIG. 7A through FIG. 7C are examples of a display screens that provide support for clinicians when performing occlusion tests or validating a Pes sensor.
Figure 7B:
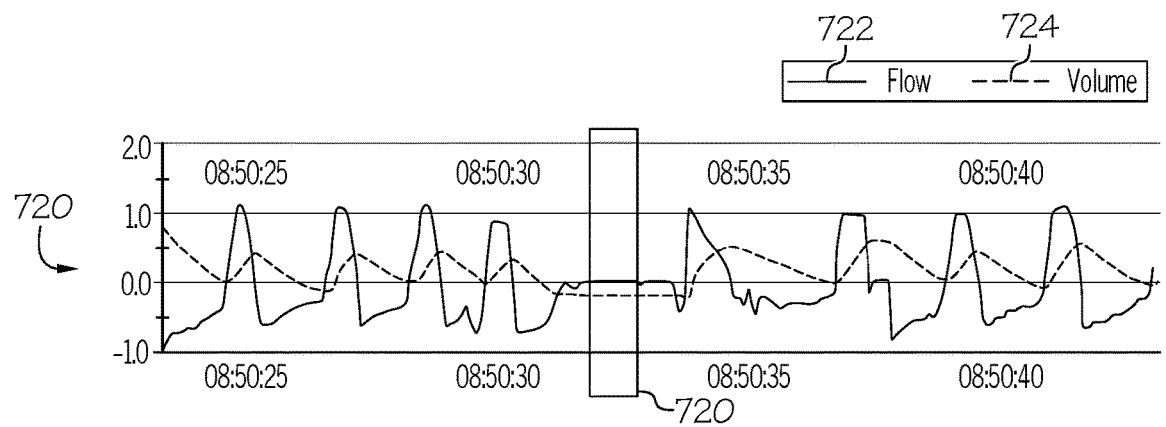
Figure 7C:
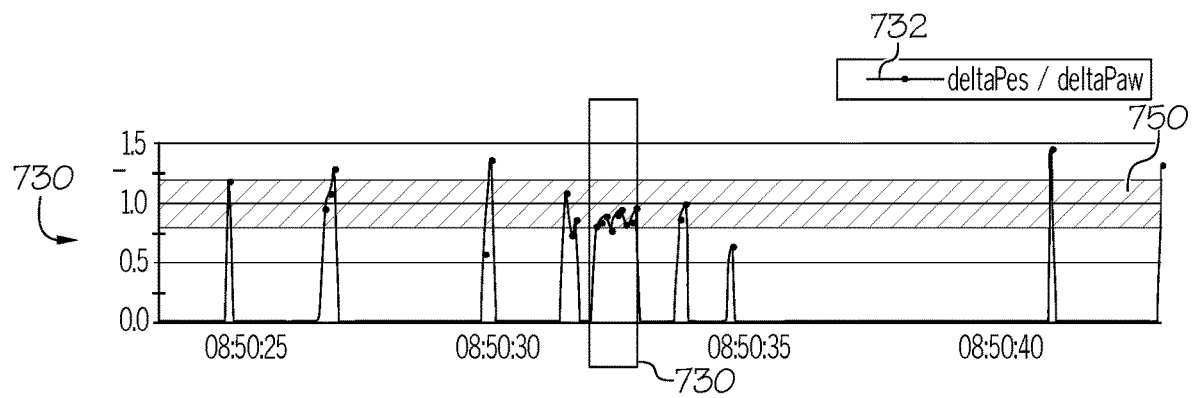

FIG. 7A through FIG. 7C are examples of a display screens that provides support for clinicians when doing occlusion tests or validating a Pes sensor. The top plot in FIG. 7A shows the esophageal pressure and airway pressure simultaneously. This is important because a successful occlusion test results in pressure drops in esophageal and airway pressure that are nearly identical. The second plot in FIG. 7B shows flow and volume. It is important for an occlusion to be airtight, and thus there should be no flow during the occlusion. The third plot in FIG. 7C shows the ratio of the change in esophageal pressure divided by the change in airway pressure. This ratio should be approximately 0.8 to 1.2. This area is highlighted in hatched pattern 750 (i.e., green range) to indicate a good occlusion test. The system is smart enough to only show this ratio when flow is zero or near zero to improve visual interpretation of the chart. The box 710, 720 and 730 in each diagram in the diagram points out the good portion of the occlusion test where airway pressure and Pes are dropping, flow is zero, and the ratio of Pes and Paw are close to 1. Also of note in this figure is the trigger time before each breath. The trigger is shown as a Paw pressure dip when the patient starts to inhale but the ventilator has not yet turned on the positive flow to support the breath. As shown in the figure, the slope of the airway pressure curve and the esophageal pressure curve during this time is nearly identical indicating that the Pes sensor is likely producing good data.

Figure 8A:
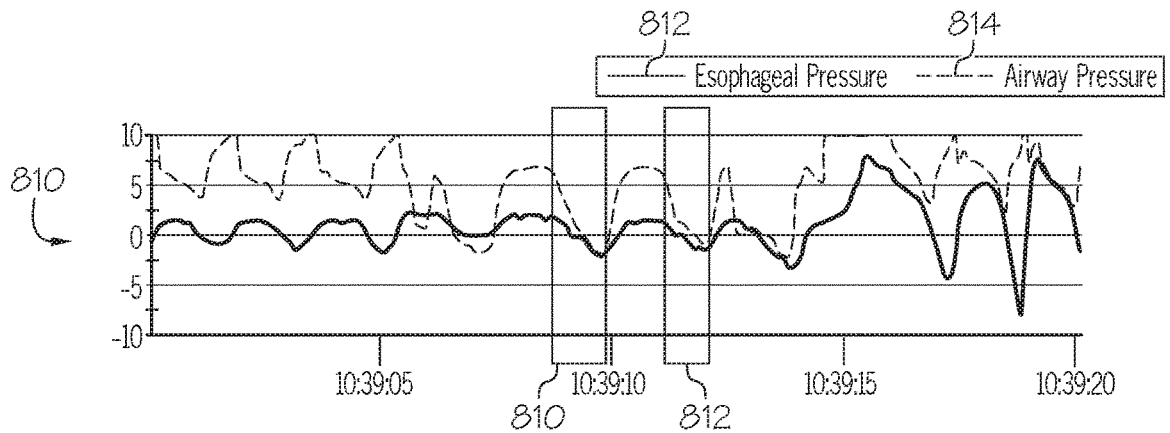
FIG. 8A through FIG. 8C are examples of a display screens that provide support for clinicians when performing occlusion tests or validating a Pes sensor, except the occlusion test is poor.
Figure 8B:
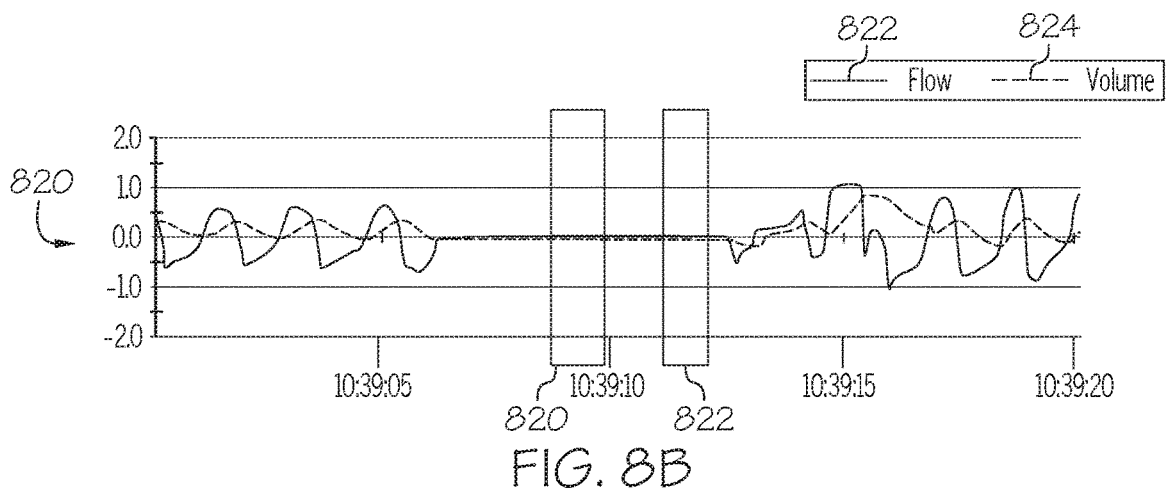
Figure 8C:
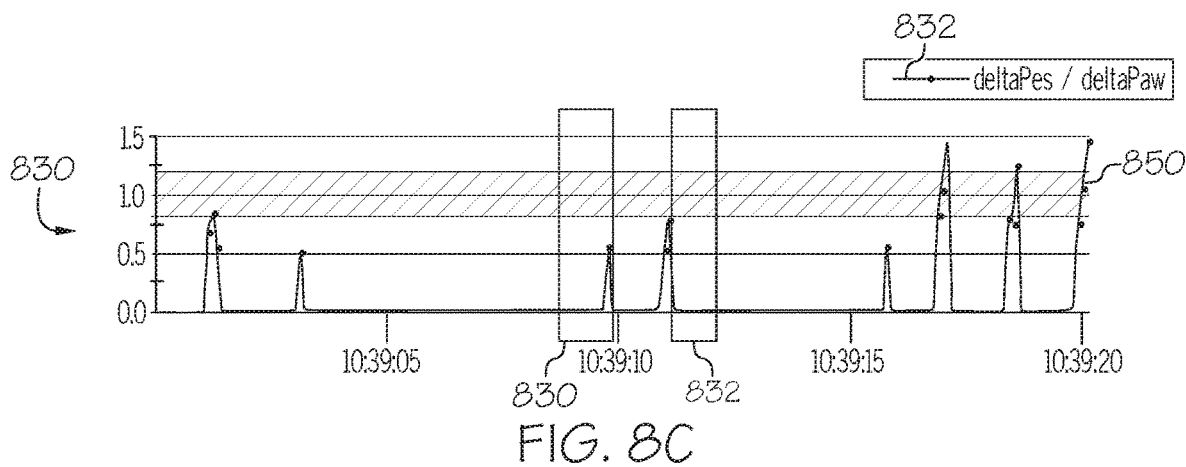

FIG. 8A through FIG. 8C is a similar FIG. 7A through FIG. 7C, except the occlusion test is poor. The flow is zero, but the Pes does not drop nearly as much as the airway pressure, therefore the Pes/Paw ratio never gets into the green range (i.e. hatched pattern 850) in regions denoted by boxes 810, 812, 820, 822, and 830, 832.

Clinical Decision Support Tool for Safe PEEP

Figure 9:
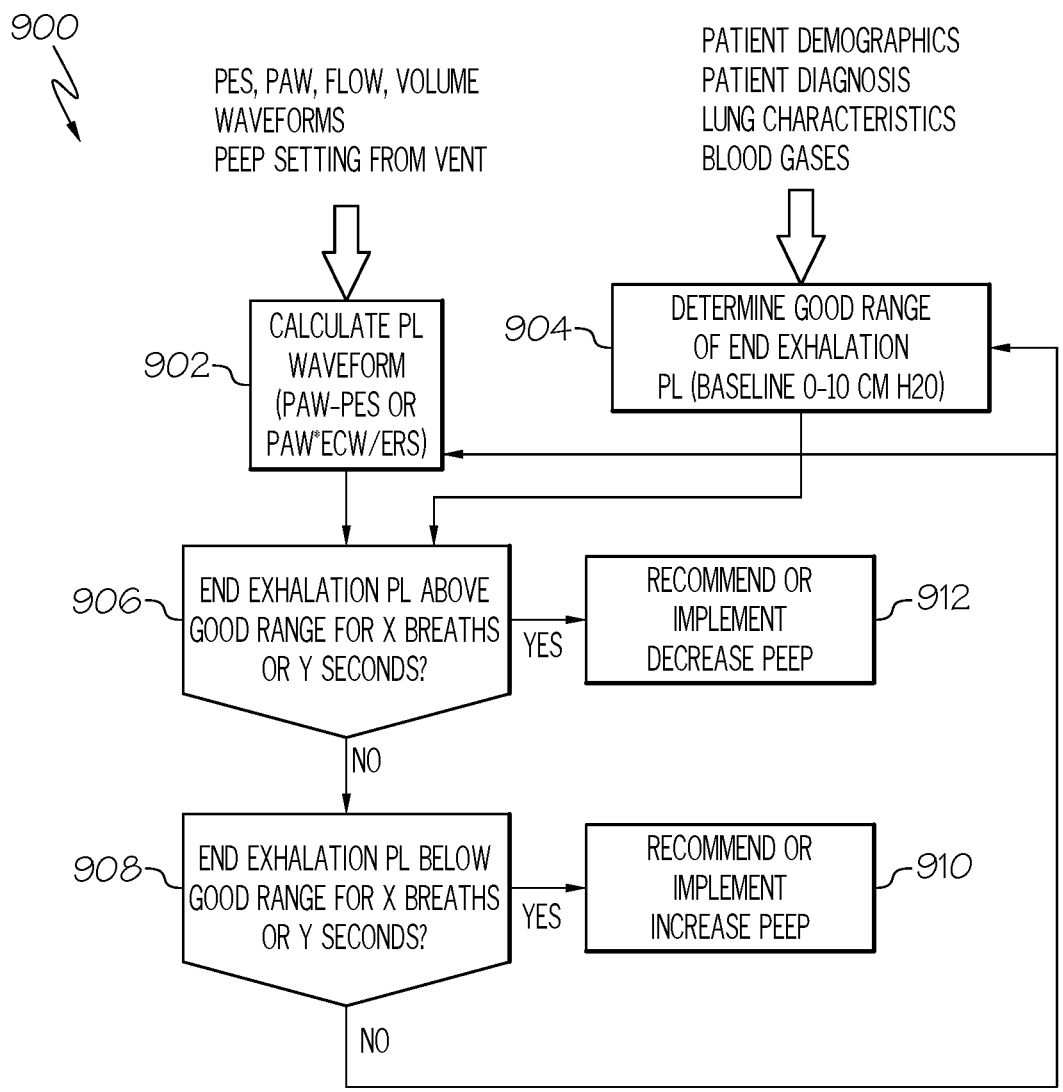
FIG. 9 is a flow diagram of clinical decision support tool for optimizing or maintaining safe PEEP levels.

FIG. 9 is a clinical decision support tool 900 for optimizing or maintaining safe PEEP levels. In step 904, the good range of end exhalation PL is calculated from the patient, clinical best practices, demographics, diagnosis, lung conditions and/or blood gases. Higher levels of PL may be necessary in sicker patients or patients with low PaO2/FIO2 ratios (indicating poor gas exchange). In healthier patients, lower PL values would provide more protection to the lungs. However, PL values below zero may also induce lung stresses from opening and closing alveoli, which should also be avoided. In step 902, using the waveforms, PL is calculated (multiple possible methods) and compared to the "good range" determined previously. In step 906, if end exhalation PL is above the good range for a series of breaths or time, then in step 912 the system would implement or recommend a decrease in PEEP to lower end exhalation PL. In step 908, if end exhalation PL is below the good range for a series of breaths or seconds, then in step 910, the system would recommend or implement an increase in PEEP to raise the end exhalation PL. The good range may also change over time as the lung conditions and gas exchange improve or deteriorate over time (indicated by blood gases or physiologic models or changing diagnosis). In addition to adjusting PEEP based on PL and on exhalation parameters, peak PL should also be monitored to ensure that the patient is obtaining sufficient volume of gas at sufficiently low pressures to protect the lung.

Clinical Decision Support Breathing Support

Figure 10:
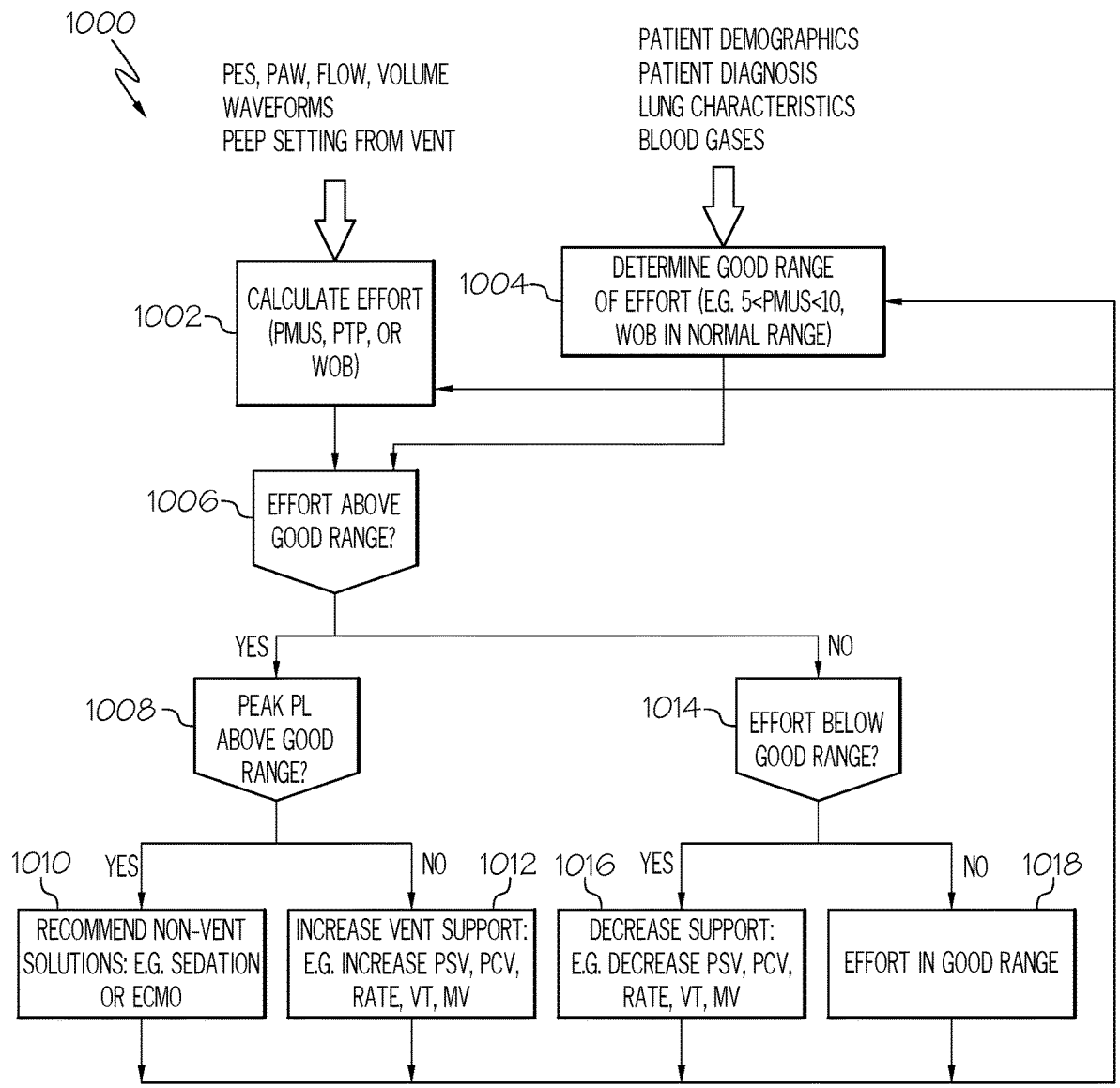
FIG. 10 is a flow diagram of a clinical decision support for spontaneous breathing support based on Pes sensor.

FIG. 10 is clinical decision support tool 1000 for spontaneous breathing support based on Pes sensor. Based on clinical best practice, patient demographics, diagnosis, lung conditions and/or blood gases, determine the range of acceptable effort. Some clinicians think having Pmus between 5 and 10 is adequate to maintain muscle strength but not stress the patient or the lung. Normal ranges of WOB may also be used (typically between 0.3 and 1.0 J/L). These ranges should be adjusted based on the patient demographics, diagnosis and/or lung conditions (very sick patients or very old patients may not be capable of or accustomed to breathing as hard as some very healthy patients or COPD patients who work hard normally). In step 1002, the patient effort can be calculated via the Pes waveform and in some cases also using flow and volume. For example, work of breathing (WOB) is calculated using the Campbell diagram which integrates Pes and volume using chest wall compliance which is calculated using Pes, paw, flow and volume during passive breathing. In step 1006 a test is made. If the breathing effort is too high, in step 1008 the next check is to see if PL is near to or higher than acceptable for lung protection. If it is, in step 1010 adding more ventilator support may make this worse and other solutions such as sedation or ECMO may be suggested. If not, in step 1012, increasing ventilator support would be recommended or automatically implemented (in the form of increasing PSV, increasing rate or tidal volume, or increasing other support methodologies). If the effort is too low in step 1014, this could lead to disuse muscle atrophy. In step 1016, decreasing pressure support or other ventilator support should induce more effort by the patient. In addition, sedation could be lowered to increase patient effort. Otherwise the effort is good in step 1018. The whole process repeats as often as each breath, but most often times the system uses averages (e.g. last 10 breaths) to avoid over reacting to a few outlier breaths.

In addition to just using effort to adjust the ventilator, PetCO2, minute ventilation, and oxygen saturation also play an important role in setting the ventilator. Mode changes, changes to respiratory rate, triggering, tidal volume and other adjustments can be made to optimize ventilation while maintaining good effort and adequate lung protection.

Adaptive Filter for Pes Waveform

Figure 11:
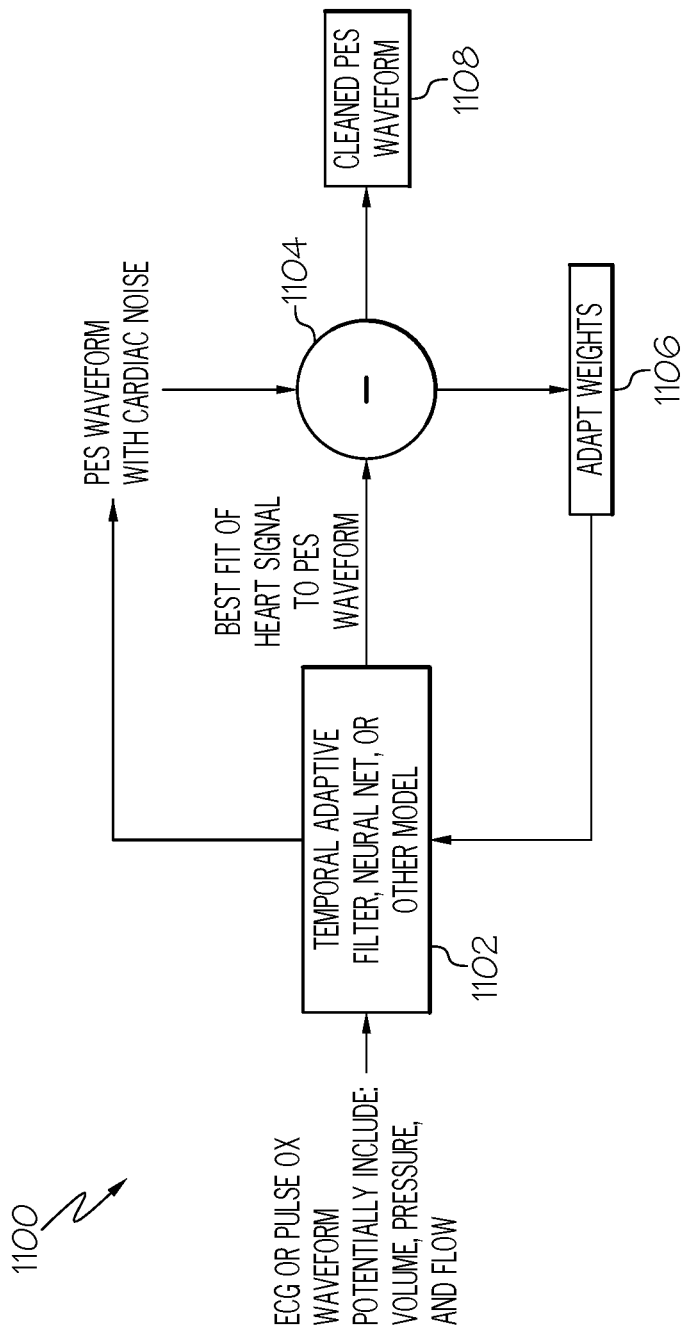
FIG. 11 is a diagram of an adaptive filter that is used to clean the Pes waveform of cardiac (cardiogenic) noise.

FIG. 11 is a diagram 1100 that shows an adaptive filter that is used to clean the Pes waveform of cardiac (cardiogenic) noise. Using the ECG or pulse ox waveform, a temporal adaptive filter 1102 (neural network or other non-linear or linear adaptive model) is trained to modify the cardiac waveform to best match the cardiac noise in the Pes waveform. Since the ECG/pulse-ox signals are independent of the breathing signal, the only portion of the Pes waveform that will match the ECG/PulseOx is the cardiac noise. Subtracting 1104 the output of the adaptively modified ECG/PulseOx signal from the Pes signal produces a clean(er) Pes waveform free from cardiogenic noise 1108. The output of the adaptive filter may need to be filtered or smoothed before or after the subtraction to minimize artifacts. This cleaner signal can be used to trigger the ventilator or better implement the myriad of capabilities provided by the Pes signal. The weights of the temporal adaptive filter/model are adjusted continuously by machine learning algorithms that attempt to minimize the error between the dirty Pes waveform and the cardiac waveform. Various least squares algorithms are commonly used in this situation. Since the only commonality between the dirty Pes signal and the cardiac signal is the cardiac noise in the dirty Pes signal, the machine learning algorithm will modify the output of the adaptive model to most closely match the cardiac noise found in the dirty Pes signal. When the best match of the cardiac noise is subtracted from the dirty Pes signal, a Pes signal with optimally removed cardiac noise is achieved. The volume, pressure or flow in the lung at different stages of breathing may attenuate the cardiogenic noise in the Pes. Thus, adding these values to the adaptive filter/model may improve the output of the system. However, since those airway signals correlate with the Pes signal, care must be used to ensure that true Pes data is not removed during the cleaning process.

Adaptive Filter for Paw and Flow Waveform

Figure 12:
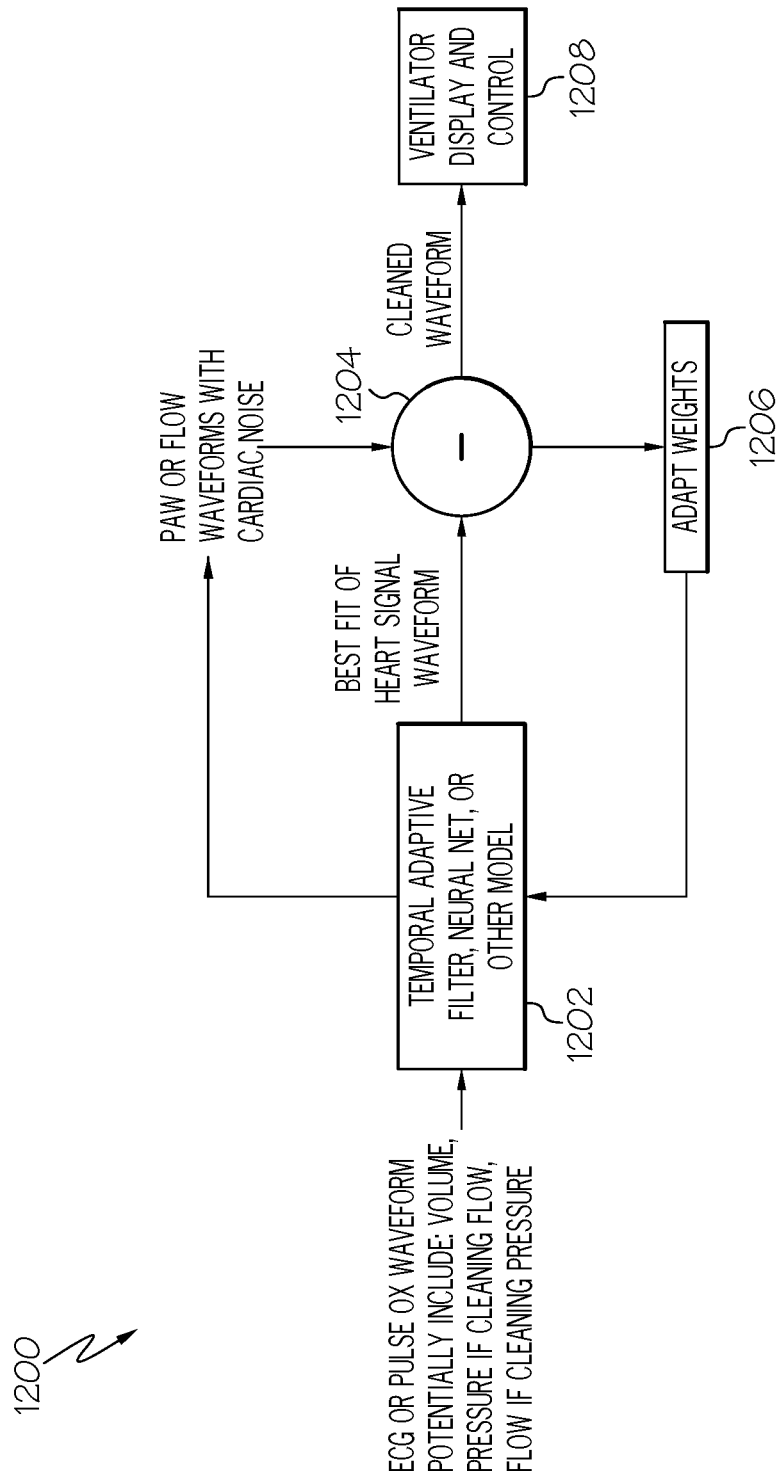
FIG. 12 is a diagram of an adaptive filter that is used to clean the Paw or Flow waveform of cardiac (cardiogenic) noise.

FIG. 12 is a diagram of an adaptive filter that is used to clean the Paw and Flow of cardiac (cardiogenic) noise. With reference to description for FIG. 11 above features 1202, 1204, 1206 and 1208 perform similar function. The ECG or PulseOx waveforms can be matched to the cardiogenic noise as described above to provide a cleaner version of the signal. This could be critical in avoiding false triggering and asynchrony sometimes caused when the cardiogenic noise is quite large.

Figure 13A:
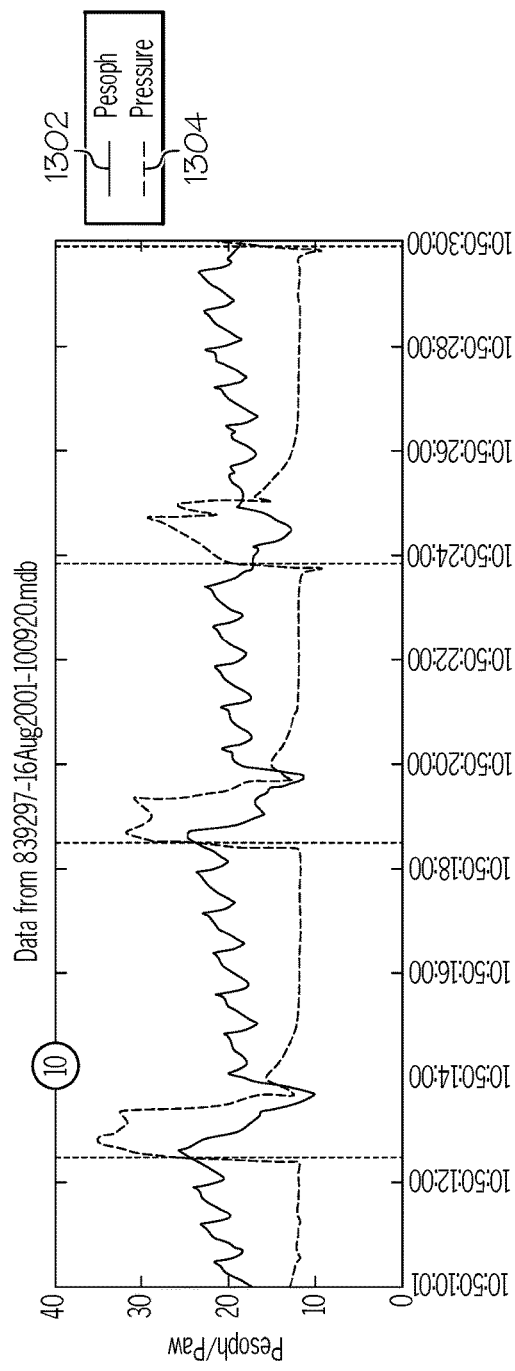
FIG. 13A is a diagram of an example of an esophageal pressure waveform and airway pressure waveform with cardiogenic oscillations.
Figure 13B:
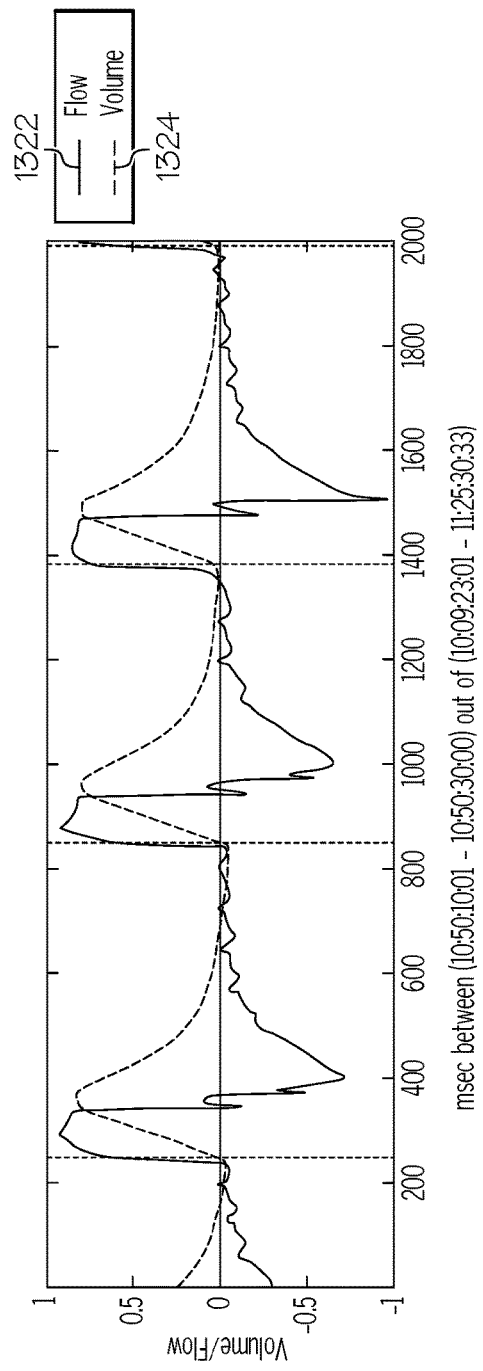
FIG. 13B is a diagram of flow waveform and volume waveform during the same time period of FIG. 13A.

Esophageal Pressure Trace, Airway Pressure, Flow and Volume with Cardiogenic Oscillations FIG. 13A is a diagram 1310 of an example of an esophageal pressure waveform 1402 and airway pressure waveform 1304 with cardiogenic oscillations. FIG. 13B is a diagram 1320 of an example of flow waveform 1322 and volume waveform 1424 during the same time period of FIG. 13A. Notice also there are small contributions of the cardiogenic oscillations in the flow waveform 1322 and airway pressure waveform 1304.

Figure 14A:
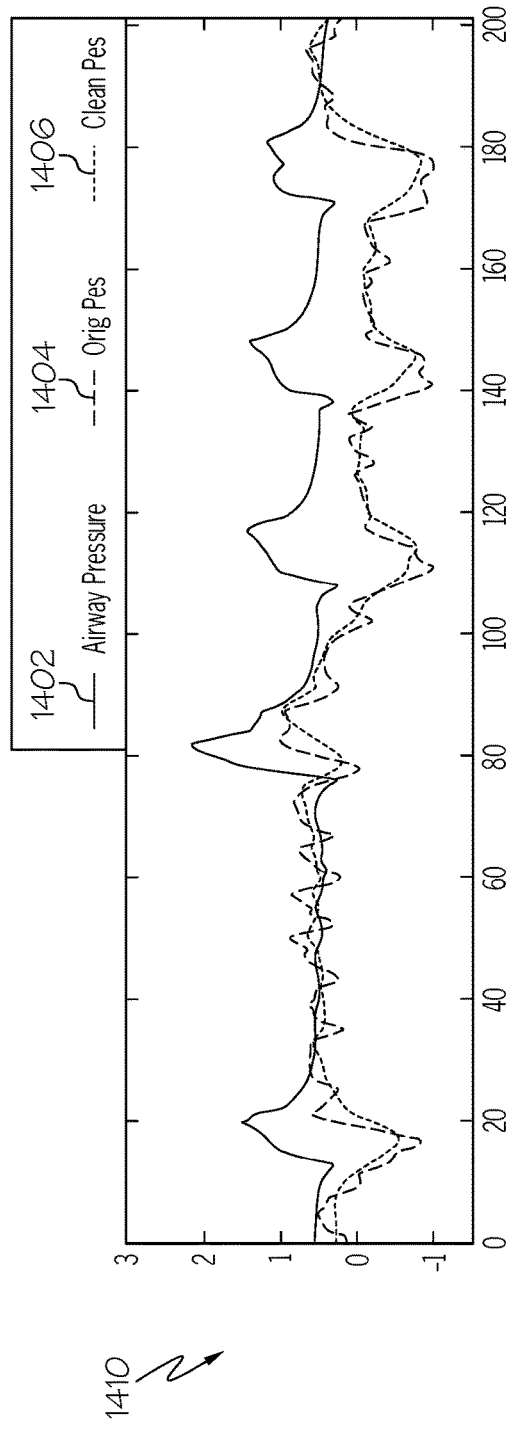
FIG. 14A is a diagram in which the airway pressure waveform and esophageal pressure waveform that has cardiogenic oscillations also showing a cleaned Pes waveform.
Figure 14B:
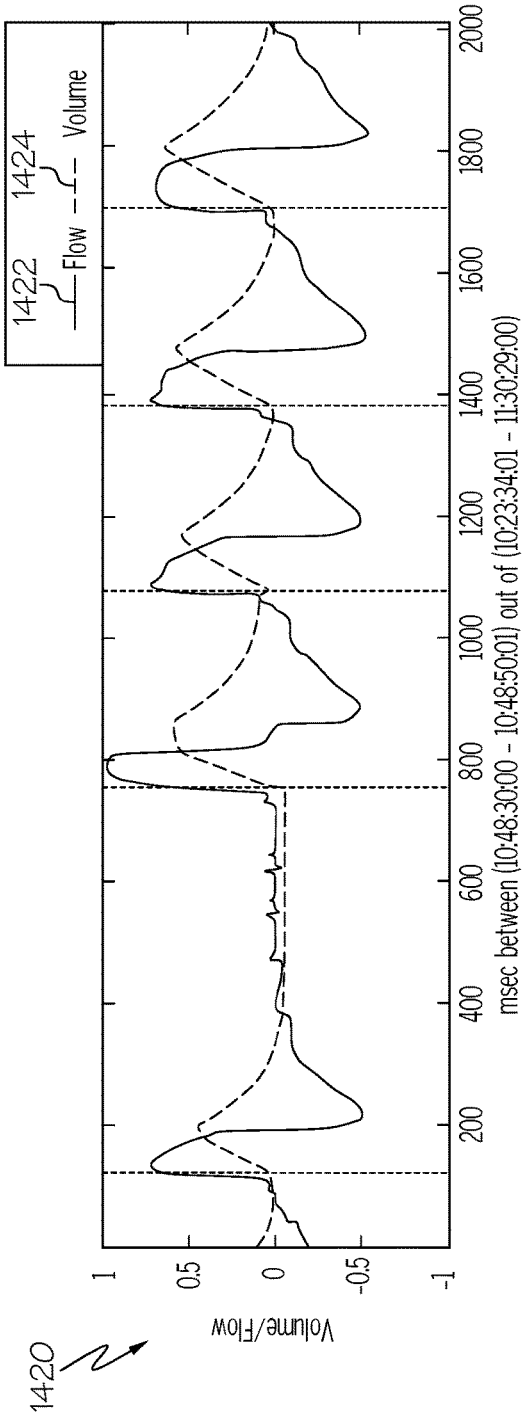
FIG. 14B is a diagram of flow waveform and volume waveform during the same time period of FIG. 14A.

Esophageal Pressure Trace, Airway Pressure, Flow and Volume with Cardiogenic Oscillations FIG. 14A is a diagram 14510 in which the airway pressure waveform 1402 and esophageal pressure waveform 1404 has cardiogenic oscillations. The cleaned waveform is shown as 1406 after cleaning the esophageal pressure waveform 1404 with an adaptive filter as described above with reference to FIG. 11. The clean waveform 1406 shows the new Pes trace that is much easier to interpret and use. FIG. 14B is a diagram 1420 of an example of flow waveform 1422 and volume waveform 1424 during the same time period of FIG. 14A.

Diagram of Pressure Volume Curve of Lung with Increasing PEEP Values

Figure 15:
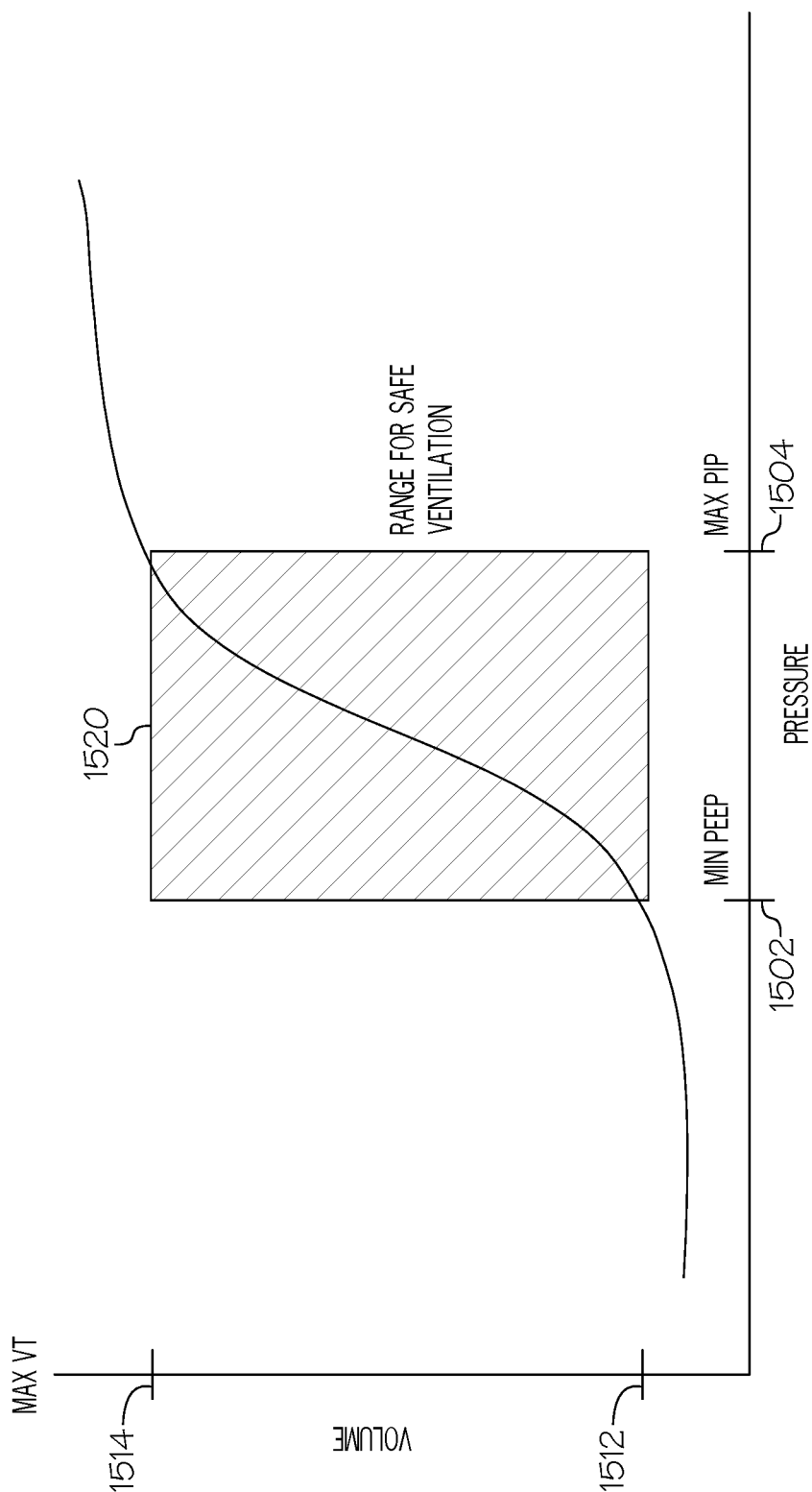
FIG. 15 is a diagram that shows the pressure volume curve of the lung with increasing PEEP values.

FIG. 15 is a diagram 1500 that shows the pressure volume curve of the lung with increasing PEEP values. The initial and final flat portions of the curve show high pressure changes with low volume changes and should be avoided. The middle portion 1520 defines the location where normal tidal breathing should occur and also defines the minimum value of PEEP. The maximum value of PEEP is that which keeps the max PIP with normal tidal breathing inside the safe region. As such, max PEEP is related to breathing pattern and lung compliance curves.

Figure 16:
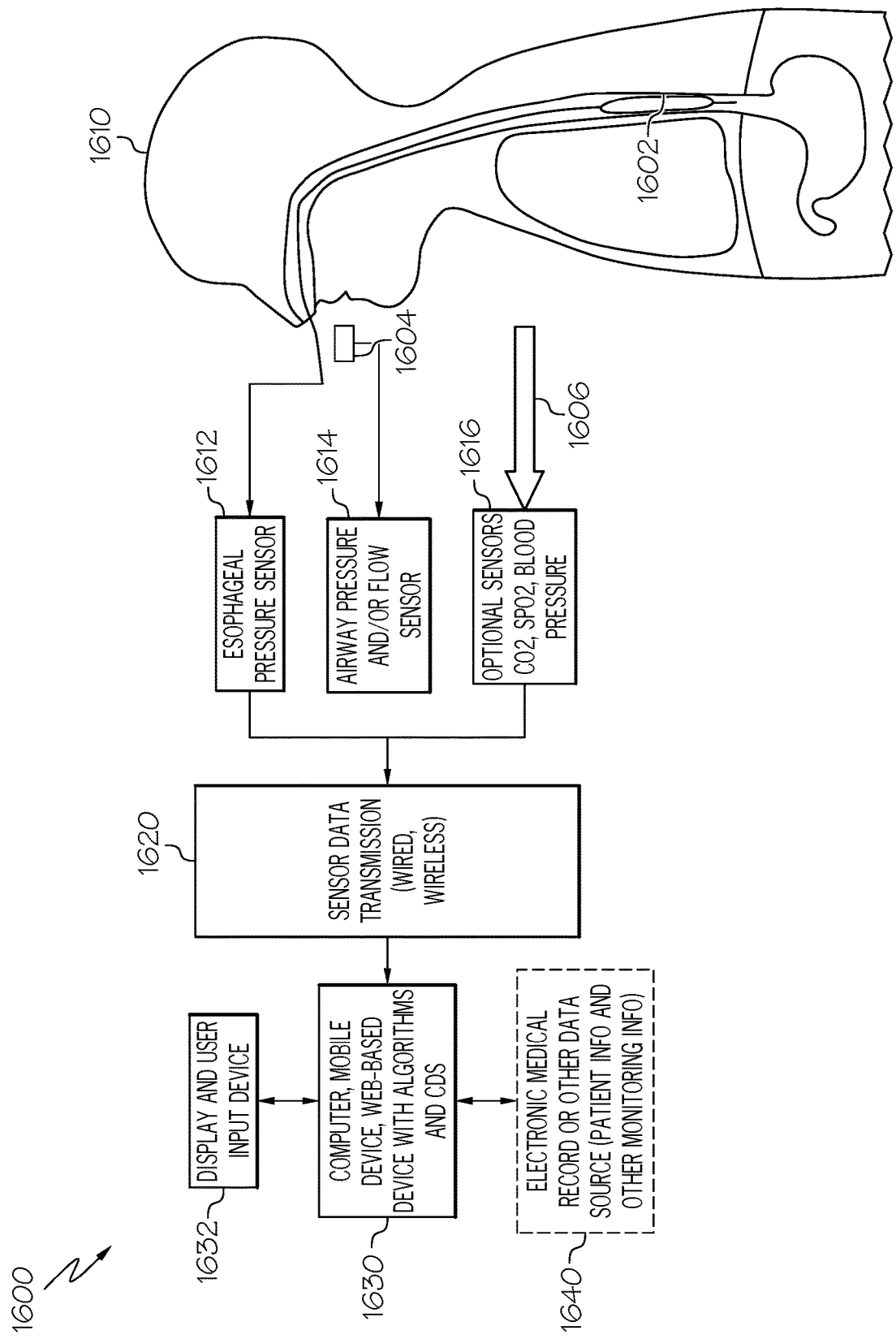
FIG. 16 is a block diagram of the system, the esophageal pressure sensor, airway pressure and flow sensor, and other optional sensors including CO2 sensor, pulse-oximetry sensor, and blood pressure sensor, are connected either wirelessly or wired to a module that transmits the data to a computer.

Example of First System for Esophageal Pressure Sensor, Airway Pressure and Flow Sensor FIG. 16 is one embodiment of the system 1600. The system includes an esophageal pressure sensor 1602, airway pressure and flow sensor 1604, and other optional sensors 1606 including CO2 sensor, pulse-oximetry sensor, and blood pressure sensor on patient 1610. The sensors 1602, 1604, and 1606, are connected either wirelessly or wired to a module 1612, 1614, 1616 that transmits the data 1620 to a computer, mobile device, web-based device or service or other computing system 1630 that can implement the computer decision support and algorithms described herein. The computing device accepts the data from the sensor transmission module along with data from the clinician via a user interface 1632 (e.g., patient position) and possibly data from the electronic medical record (patient diagnosis, patient medications, patient lung health, patient demographics such as height, etc.), physiologic monitor (blood pressure, $Co_2$, ECG, etc.), and/or ventilator (ventilator sensors or settings) 1640. The algorithms and clinical decision support code can run on a mobile phone, tablet, laptop or desktop computer or as a web service when connected to the sensors and a method of receiving data from those sensors. The algorithms, CDS, Sensors and Sensor data and display/user-input can all be built into a single medical device that functions as a smart respiratory monitor. The CDS and algorithms could also be embedded into an existing physiologic monitor or into the electronic medical record system, as long as the sensor data could be received there.

Figure 17:
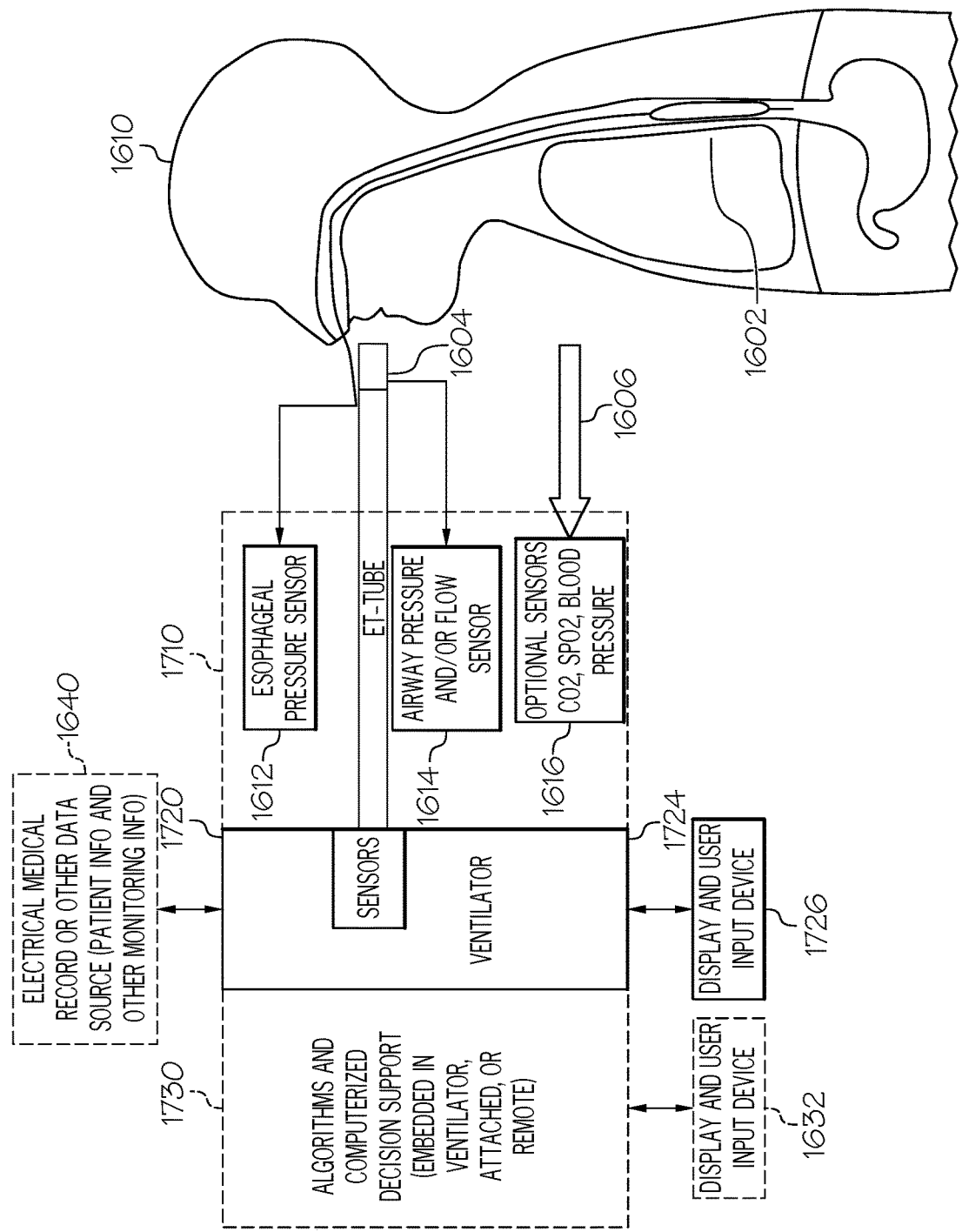
FIG. 17 in another embodiment, the ventilator optionally includes one or more of the sensors needed.

Example of Second System for Esophageal Pressure Sensor, Airway Pressure and Flow Sensor FIG. 17 is another embodiment system 1700. The components are identical to those described in FIG. 16. The ventilator 1720 optionally includes one or more of the sensors needed. The airway adapter could be replaced and use the internal ventilator pressure and flow sensors inside the ventilator at the ventilator end of the ET-Tube. The algorithms and CDS 1730 could be embedded into the ventilator, or could be embedded into another device that receives data from the ventilator instead of directly from the sensors. The optional EMR data, physiologic monitoring data, display and user interface data could be obtained from the ventilator, or directly to the device attached (wired or wirelessly) to the ventilator. Again, the algorithms could obtain all the data necessary from the ventilator and could be embedded into an EMR, physiologic monitor, separate medical device, or standard computer or mobile device or web service.

Decision Support System

Disclosed is a clinical decision support system for ventilating a patient, and in particular for setting up and using an esophageal pressure sensor system. As described above, using esophageal pressure for improved surveillance and adjustment of the ventilator is difficult for several reasons including:

Placing the Pes system requires experience and skill that not all clinicians possess Proper inflation of the Pes system is difficult and varies with balloon type and patient characteristics Pes data is sometimes noisy, complicating interpretation and use Interpreting the data associated with Pes measurement is sometimes difficult Maintaining the Pes system in proper working order (placement and inflation) and knowing that the Pes is accurately being measure is difficult to do continuously.

Setup of the Pes Sensor System

Determining when the Pes sensor system is setup correctly is often difficult and takes a level of skill. As exemplified in FIGS. 7 and 8, the Pes CDS can create an enhanced user interface for supporting the proper set up of the Pes sensor system. Showing both Paw and Pes on the same graph and also a dynamic ratio of the change in Pes versus the change in Paw will allow the clinician to quickly and easily determine if the sensor is working properly. A good occlusion test prevents flow from reaching the patient, so a plot showing flow or an indicator showing very low or zero flow is also useful. Ideally the ratio of the change in Pes versus the change in Paw during a maneuver is close to 1, however when the patient is in the supine position, the ratio is often less than 1. A green region near 1 (e.g., preferably 0.8 to 1.2 or 0.9 to 1.1) can be shown such that if the pressure drop in the two sensors matches within 10% or 20% for a certain amount of time during the occluded inspiration (when flow is low or zero and pressure is changing), the system can graphically show that the sensor is working properly. This region can be adjusted based on patient position if necessary. In another embodiment, instead of displaying the ratio of Pes to Paw, the display could plot Pes versus Paw on a graph. Ideally, the graph will show a slope of 1, but slopes between 0.8 and 1.2 are likely acceptable. Again, a green range of the appropriate acceptable slopes could be shown to help the clinician interpret the results of the occlusion test. The Pes CDS can automatically interpret the data to continuously notify the clinician directly when the two sensors are matching well. Typically an occlusion test is implemented by occluding the airway (either manually or via the ventilator) and comparing the Pes and Paw waveforms during a patient inhalation (effort). If the patient is paralyzed, clinicians can also place gentle pressure on the patient's abdomen and see an increase in pressure in both waveforms. Either method can be used with the CDS methodology. This process is outlined in FIG. 4.

During setup, the Pes CDS can monitor the Pes and determine if the sensor is too close to the heart (e.g. needs to be lowered further into the esophagus). When the Pes shows large cardiogenic oscillations (pressure changes due to the beating of the heart as shown in FIG. 14), the esophageal sensor can be lowered closer to the stomach to minimize the cardiogenic oscillations. If ECG, pulseoximetry (PulseOx), or other measurements of cardiac activity are present, the non-breathing oscillations in the Pes can be matched to the cardiac activity sensor to ensure that the artifact in the Pes signal is actually from the heart (differentiate between cardiogenic oscillations and potentially high rate of effort to breath creating ineffective triggers). In addition to validating that the oscillations are coming from the heart, the cardiac sensor can be used to clean the Pes signal of cardiac noise using matched or adaptive filtering techniques (more detail later). If cardiac sensors are not available, the non-breathing oscillations in the Pes signal can be compared to standard heart rates (40-120 BPM), which are typically much higher than respiratory rate. In addition, high frequency breathing oscillations should be synchronized to the ventilator breathing pattern whereas cardiogenic noise should be independent from the breathing pattern, thus assessing the location of the oscillations can be used to separate small, rapid breathing efforts from cardiogenic noise. If the noise from the Pes signal is judged to be cardiac in nature, and the noise is higher than a threshold pressure (e.g. 2 cm $H_2O$), than the Pes CDS can recommend to move the catheter further down.

Similarly, when the esophageal pressure sensor is placed too low, the sensor goes into the stomach and the waveforms become inverted with breathing. This can be detected by comparing the Pes measurements with the Paw measurements. During spontaneous breathing, Pes should drop during the trigger and early part of the breath and gradually rise back towards baseline at the end of the breath. When the sensor is in the stomach, the Pes waveform will track more directly with the Paw measurements. If this pattern is detected in the data, the system can recommend that the sensor be repositioned away from the stomach (sensor pulled back or up the esophagus). An example outline of this process is shown in FIG. 5.

The goldilocks position of the Pes sensor is low enough to minimize cardiogenic noise but high enough to avoid being in the stomach while also accurately capturing equivalent pleural pressure. (FIG. 3) Some clinicians suggest starting by moving the catheter all the way into the stomach and then pulling it back until you just begin getting cardiac artifacts. Decision support could help the clinician perform these maneuvers. After initial placement and balloon inflation (if using a balloon), the system could ask you to lower the catheter until the system detects (using waveform analysis to detect the shift from pleural pressure to gastric pressure) that at least part of the catheter is in the stomach. This is detected when the Pes waveform follows the airway pressure waveform during spontaneous breathing. At this point, the clinician is instructed to start gently pulling back on the catheter until the system detects cardiac artifacts in the Pes waveform. This is detected by either looking for artifacts at approximately the right frequency (40-120 BPM) or by using an available ECG or pulse-oximetry system to match the heart rate to the detected artifact. When this is completed, the system could then turn on the "cardiac artifact rejection" algorithm (see below) to smooth the waveform.

Continuous monitoring of the raw Pes waveform (unseen if cardiac artifact rejection is turned on) can be done to ensure a small and consistent amount of cardiac artifact is present in the signal, thus indicating correct placement. If incorrect placement is detected (large or absent cardiac artifacts), instructions to the clinician can be provided to reposition the sensor. The placement process described above could be repeated, or the system could ask that the clinician slightly pull back or push in the catheter until the situation is resolved. Similarly, other standard procedures for placement of the esophageal sensor can be supported by the Pes CDS, particularly using data from the waveforms collected during placement of the sensor.

In addition, detection of inaccurate or untrustworthy Pes (balloon not inflated properly, sensor placed in the wrong location, doesn't match airway pressure like it should, or other situation that indicates the Pes is not trustworthy) can lead to the blanking, shading, or marking of any data derived from the Pes such that the clinician will know that the data is potentially no longer trustworthy. Similarly, if decisions are being made by the ventilator/monitor or Pes is being used in a closed loop system or derived parameters are being calculated, then these facilities could be turned off or shown differently to protect the patient and alert the clinician. If an esophageal sensor monitor is external to the ventilator, it can send a signal to the ventilator to indicate untrustworthy data, or simply display an indicator that the Pes sensor should not be trusted.

Proper Pes Balloon Inflation

When esophageal balloons are used, clinical decision support for balloon inflation is possible. Typical best practice is to inflate the balloon using a 10 ml syringe. The starting point for balloon inflation is dependent on the type of catheter but often times is around 4-6 ml of air. Other catheters may use as little as ½ ml (or cc) of air. A CDS would use a lookup table based on type of catheter to indicate how much air should be inflated. Similarly, the catheters could have an RFID or other keying methodology (in the connector, electronic, etc.) to determine the type of catheter and allow for correct guidance, decision support, or closed loop behavior. However, different catheters, physiology and different breathing patterns may indicate the need to adjust the amount of air in the balloon on a patient-by-patient basis or even intra-patient when ventilator settings or patterns change. For example, a patient with high spontaneous drive to breathe (high WOB) may require less air in the balloon. Whereas, a passive patient with high lung pressures and Pes may require more air in the balloon. When the esophageal pressure is negative, the balloon will expand as it draws in air from the tubing. If the balloon is overinflated, the size of the balloon (relative to the esophagus) will limit the amount of expansion and limit the ability to measure high negative pressures. Similarly, when the Pes is positive, the pressure will force air out of the balloon and into the tubing, creating positive pressure in the sensor. If the balloon is underinflated, the balloon will completely collapse and will not be able to measure the full scale of the positive pressure. Both of these situations can be seen as a rapid nonlinearity or thresholding of the Pes measurement.

In particular, if the waveform shows a flattening of the Pes that occurs at almost identical pressures in multiple breaths, the balloon is likely improperly inflated. If the flattening only occurs in one or a couple breaths and other nearby breaths exceed this pressure (positive or negative), it is not likely due to poor balloon inflation. A Pes CDS can detect these patterns in the signals and recommend that the clinician adjust up or down the amount of air in the balloon. This monitoring can be done continuously as well as during the initial placement allowing for the detection of slow leaks or changes in physiology or other factors that may eventually create inaccurate Pes measurements.

In another embodiment, the Pes CDS contains a lookup table of the different types of balloon catheters and their minimal nonstressed volume, believed to be the ideal inflation point for most catheters. The clinician can be directed to insert the correct volume and then the fine tuning described above can be used to ensure the optimal volume is used. The Pes CDS can also automatically calculate the elastic pressure of the esophagus imposed by filling the balloon and subtracting that pressure from the Pes signal.

In another embodiment, the balloon inflation can be done automatically with a source of gas. For example, the device can be inflated using a small pump, compressed gas, or gas from a compressor in or powering a ventilator. The automatic inflation can mimic the procedure implemented by the clinician by first inflating the balloon based on a table lookup and then watching the data from the occlusion test and dynamic breathing to determine if the balloon requires more or less air. This is particularly important in some cases where the balloons may have small leaks that will gradually allow the air to leak out and Pes measurements to go bad. Using Pes measurements to automatically adjust the ventilator settings can create significant problems if the Pes is not always accurate.

In addition, the Pes CDS can automatically adjust the clinical recommendations or Pes signal to correct for a variety of situations that might occur. For example, a supine patient has lower Pes values than upright patients. Some of this is real, and some is an artifact of forces on the pressure sensor. As such, a correction factor can be applied to the pes signal based on patient position. In healthy subjects, the change in PL is lower than in sick patients, so Pes and PL measurements may also be altered by diagnosis as well as position.

Device Can Continuously Monitor Performance of the Pes Sensor

The methodology of detecting when the balloon is over/under inflated or the sensor is placed properly in the esophagus can be utilized during initial placement and setup of the Pes sensor, but also used during continual use of the sensor to ensure the sensor continues to have the correct amount of pressure/volume and is in the right location. The Pes CDS can watch the Pes tracings continuously to determine if there is ever a problem with the Pes sensor.

In one embodiment, the Pes sensor can be validated continuously during operation using the trigger time. In ventilators that support spontaneous breathing, the ventilator must use a pressure or flow sensor to detect a spontaneous effort and then respond by providing gas to the patient. The time between the start of the patient's spontaneous breath and the ventilator providing flow is called the "trigger time" because it is the time required for the patient/ventilator to trigger a breath. During this time (after the previous exhalation and before the next start of ventilator flow) the airway is often occluded to allow for rapid detection of spontaneous effort. This trigger time behaves as a miniature occlusion test before every breath that can be used to analyze the behavior of Pes and Paw. Although it is not long enough to completely characterize the performance of the Pes signal (like was described above in an occlusion test), it is long enough to ensure that the balloon is functioning reasonably well. In addition, trends in the Pes/Paw relationship can provide insight into whether the balloon is still functioning as well as it was during the previous occlusion test. For example, because of the short duration of the trigger time, a perfect 1:1 match of the change in Pes versus the change in Paw during the trigger may not be possible. However, a trend from 0.8 to 0.6 to 0.4 may indicate that the balloon is deflating, moving, or needs attention.

The ventilator trigger time can be extended for data that more closely approximates an occlusion test by simply changing the sensitivity or triggering settings on the ventilator (making it slower to respond to breathing efforts). This can be done manually, can be recommended by the CDS when the CDS suspects a change in Pes performance, or can be done automatically (for example, one breath every few minutes) if the system is built into a ventilator. A preferred embodiment would be to have the ventilator automatically impose a long trigger time periodically (e.g. once per 5 minutes) to check the performance of the sensor. Occlusion tests are uncomfortable for the patient and often times require clinician intervention. Using the trigger settings to impose short duration and periodic occlusion tests can enable the long-term, reliable use of Pes. This enables continuous analysis of synchrony, lung protection (e.g. trans diaphragmatic pressure monitoring), work of breathing, and improved triggering in ventilators using the Pes signal. Similarly, end expiratory pause or end inspiratory pause can be used to create an occlusion event periodically during ventilation for evaluation of the Pes signal.

Device Can Clean Noise From Pes Sensor

Even a correctly placed esophageal sensor may have some cardiac oscillations imposed on the waveform (FIG. 14). This can make triggering, analysis, or interpretation difficult, particularly when looking at fine details of the signal. Simple filtering removes a block of frequencies from a waveform, but these frequencies may also be present in the signal of interest. For example, the breath rate may be only 10 breaths per minute at times, but the characteristics of the Pes waveform including rapid rises and descents during each breath that may contain frequencies that overlap with the frequencies in the cardiac oscillations. Filtering out the cardiac noise from the Pes waveform may create an overly smooth Pes waveform that has lost some of its value. As such, an advantageous system is an adaptive filter that uses the location of peaks or the timing of the ECG or pulse ox to remove as much as possible of the cardiac signal from the Pes signal without filtering the Pes dynamics. (FIG. 11) Using a time delay neural network, recurrent neural network, linear adaptive filter, autocorrelation, cross-correlation or other temporal modeling architecture allows the filter to dynamically match and select the cardiac contributions from the signal and selectively remove those attributes without modifying the rest of the Pes dynamics, thus improving look and usefulness of the Pes signal.

Traditional adaptive filtering will create an optimal match of the contents of the cardiac noise in the Pes waveform with a heartbeat signal from ECG or pulse-oximetry by adjusting weights in the filter until the optimal offset, amplitude, and delay between the two signals is created. This optimal match can then be subtracted from the Pes waveform (often with a low-pass filter to minimize artifacts from the subtraction) to create a cleaner version of the Pes waveform. Because the cardiogenic oscillations in the Pes waveform may not be a simple linear match to the ECG or pulse-oximetry waveform, a more advanced methodology may be utilized. Nonlinear, multi-model, neural network, or other machine learning techniques can be used to produce better matches to the data. In addition, more parameters can be used to improve performance of the algorithm. For example, the size of the cardiogenic oscillations may be dependent on the volume of the lungs or the pressure in the chest. As such, adding a flow, volume, airway pressure, or similar signal to the model may improve performance. Also, changes in Pes may be offset in time from the ECG or PulseOx. This can be handled by adaptive delay of the signals, autocorrelation, or similar techniques known in the art for finding the best time delay for matching the signals. In one embodiment, waveform segments near the ECG or Pes peaks would be extracted and manipulated through averaging or similar techniques to create a best fit model of the cardiac artifact, which could then be modified dynamically via the adaptive filter approach outlined above to best match the changing amplitude and location of the artifact found in the signal. This could be important since at times the amplitude of the cardiogenic oscillation is dependent on the volume in the lungs or other breath to breath changes. FIG. 15 shows the difference between a noisy Pes with cardiogenic signals and a cleaned version created with adaptive filtering.

Similarly but in reverse, modeling the cardiogenic oscillations may provide insight into some of the parameters that affect the cardiogenic oscillations. For example, modeling the cardiogenic oscillations and their changes over time may provide insight into the level of intrinsic peep, diaphragmatic pressure in the chest, or fluid levels of the patient.

Device Can Detect Changes in Pes Signal Indicating Potential Inaccuracy or Changes in Patient In another embodiment, an algorithm can be used to ensure that the Pes signal remains valid by creating a model of the relationship between the Pes signal and other signals. For example, the Pes signal can be joined with the airway flow, pressure, and volume waveforms to create a model that detects when the Pes sensor is performing normally. In one embodiment, the algorithm would use the airway waveforms to predict the Pes sensor output. Although it is impossible to accurately predict the Pes sensor output from the airway waveforms, a model can be created that can be tracked over time. If the model gradually performs worse, or the model needs to rapidly adjust its parameters to continue tracking Pes data, then there is a change in the relationship between the airway parameters and the Pes values. This change in the relationship is likely because of poor sensor values, changing patient conditions (improving or worsening condition), or dramatic changes in ventilator settings. Warnings or notifications can be provided to the clinician when the model stops tracking or needs to adapt quickly, indicating that one of the three situations may have occurred. In some embodiments of this system, the algorithm will include past values of the signals as well as present values, allowing the algorithm to pattern match on the temporal aspects of the signals (e.g. rising/falling trends, concavity, etc.) as well as just the present values. This will likely create more accurate and useful models to better predict changes in the system. In another embodiment of the system, you may include non-waveform data such as ventilator settings like PEEP or PSV level, or you may include patient demographic or diagnosis data including conditions such as ARDS or COPD. Lastly, you could create a model that uses past values of Pes plus present and past values of other waveforms and parameters discussed above to create a model for future values of Pes. This type of system is often called a System Identification model and can be useful in determining when the system is changing or is not predictable.

Independent of the use of Pes monitoring, cardiogenic oscillations also periodically appear in airway waveforms. Similar to methods above, these artifacts can be removed from the airway pressure and flow waveforms to provide improved visual performance and also to remove potential auto-triggering based on these oscillations. Auto-triggering is a situation where the ventilator sees a pressure drop or flow rise during exhalation and thinks it is seeing the patient's effort to breath—but instead it is seeing an artifact that is not synchronized with a patient's effort to breath. By removing artifacts such as cardiac oscillations from the airway flow and pressure waveforms, auto-triggering may be avoided.

Deriving Data From Pes

In another embodiment, tracheal pressure (Ptr) can be used to provide additional information above and beyond the Pes and airway parameters. Tracheal pressure can be measured by placing a catheter with an open port or small balloon at the tip of the endotracheal tube. This catheter can be embedded into the wall of the ET-Tube and connected directly to a respiratory monitor or ventilator. If an open catheter is used, the use of a small bleed flow or occasional high pressure "puffs" may be required to keep the catheter patent since it will be exposed to mucus and other bodily fluids/materials that can clog or stick to the opening in the catheter. If tracheal pressure is included in the data, the Pes, Ptr and Paw (airway pressure) can be used along with flow and volume from the airway to make a variety of measurements. Using all three pressures, you can localize resistance and compliance to flow in the various parts of the respiratory system. For example, ET-Tube resistance can be found by subtracting Ptr from Paw and dividing by flow. This can indicate problems with the ET-tube such as kinks, disconnects, clogs, plugs, and other problems. In another embodiment, tracheal pressure can be estimated using pressure from the ET-tube cuff, which is a balloon exposed to the trachea near the bottom of the tube. Because the ET-tube cuff is inflated and may not be in the ideal state to linearly transmit pressure, the cuff pressure may need to be calibrated. In one embodiment, the points of no flow are used to calibrate the cuff pressure to mimic tracheal pressure. In another embodiment, least squares or other modeling techniques can be used to estimate tracheal pressure from cuff pressure, airway pressure, flow, volume and Pes.

Although the Pes sensor measures esophageal pressure in only one location, pleural pressure can vary in different regions of the lung, making estimation of lung stress difficult since certain regions may have higher pressures and volumes than others. In supine positions and sick patients like those with ARDS, the bottom of the lung (dependent lung region) may be as much as 10 cm higher in transpulmonary pressure than in the top of the lung (independent lung region). Spontaneous breathing also has an effect on the transpulmonary pressure, since the diaphragm is below the lung and therefore may create more stretch in the dependent lung region. Based on patient position, lung and patient conditions, chest x-ray or level of edema, level of spontaneous effort, and Pes waveforms/measurements, a model could be made to estimate changes in PL throughout the lung. This could be enlightening to clinicians who may not recognize the stress imposed on certain portions of the lung during mechanical ventilation.

Alternative Use Cases

In some patients, inserting a Pes sensor and maintaining its accuracy may be difficult. Alternative non-invasive estimates of Pes are possible, and include measures of muscle pressure (Pmus, an estimate of Pes created using the airway equation and accurate estimates of respiratory resistance and compliance), impedance tomography (imaging of lungs and respiratory muscles), EMG of the inspiratory muscles and/or diaphragm, or direct measurement of diaphragmatic movement or stimulation. Using a Pes sensor as a spot check or to calibrate the non-invasive measurement can dramatically improve the performance of the estimate and the clinician's trust of its accuracy. For example, using a Pes sensor, very accurate estimates of resistance and compliance can be calculated along with baseline pressures. These values can be used to initialize Pmus and to calibrate its performance. At that time, the Pes sensor can be removed or ignored while the more easily calculated and maintained value of Pmus can be used to determine asynchrony, triggering, PEEPi, work of breathing, and all the other features discussed in herein. Similarly, diaphragm movement (for example measured by EIT) or diaphragm electrical activity (for example measured by EMG) may indicate the relative amount of work being done by the patient, but a short duration of Pes measurement can be used to calibrate this relative value to create an actual estimate of Pes and the parameters mentioned above. Tracking these non-invasive surrogates over time and looking for changes in the waveforms or values enables a feature where the system could detect significant changes in the surrogate or airway data and thus request an additional Pes spot check to ensure the system is still properly calibrated.

In another embodiment, with or without using Pes measurements to calibrate or spot check non-invasive measurements, the non-invasive measurements can be used to estimate Pes and thus support many of the same features of the Pes CDS, even without a Pes sensor.

Decision Support Capabilities—Helping the Clinician Interpret the Pes Data

Measurement of Pes can provide important information for the onset, maintenance, and weaning of mechanical ventilation. The literature is full of references indicating the value of measuring Pes, but few clinicians do so (as discussed above). When reliable measurement of Pes is available, clinicians would benefit from a clinical decision support system that provides guidance and determines key decision making criteria based on the Pes waveform, patient conditions, and respiratory data. In another embodiment, a closed loop system could automatically implement some recommended changes, particularly in the ventilator, but also perhaps in other devices associated with ventilation like bronchodilator administration and infusion pumps.

Asynchrony Support

Patient-ventilator asynchrony occurs in many ventilated patients, especially those using non-invasive ventilation, and has been shown to worsen gas exchange, waste patient efforts, increase discomfort, and increase the duration of mechanical ventilation. The Asynchrony Index (AI) is considered the 'gold standard' method for measuring patient-ventilator asynchrony and is defined as a quantifiable measure of the mismatch between patient effort and ventilator delivery. The AI uses Pes and airway sensors to determine several classes of asynchrony, counts the major asynchronous events and divides by the number of breaths. The events are typically missed efforts (efforts by the patient to breath that are not detected by the ventilator), double triggering (when the ventilator triggers two times for one patient effort), auto-triggering (when the ventilator triggers a breath without a patient effort), cycling delay (when ventilator breath lasts long after the patient breath), and premature cycling (when the ventilator terminates the breath too early). It is reported in literature that increased prevalence of asynchrony is detrimental. High asynchrony (AI>10%, 1 event every 10 breaths) is associated with worsened outcomes and AI>30% is associated with higher mortality rates. When Pes is measured continuously during ventilation and validated by the CDS, the CDS can not only quantify and display the AI, but also provide advice as to how to fix the asynchrony.

In one embodiment, using the airway pressure, flow and volume and the Pes signal, a count of the different types of asynchrony and the AI can be automatically determined and displayed by analyzing the relationships between the different waveforms. Patient efforts are indicated by drops in Pes waveform, ventilator triggering is indicated by flow transitioning from negative or zero during exhalation to high positive flows during inhalation, missed triggers are indicated by drops in pes waveform beyond a threshold pressure and time that are not associated with a triggered breath. Similarly, other types of asynchrony can be calculated. Once the types of asynchrony are calculated and displayed, the CDS can either make recommendations to reduce asynchrony or automatically modify the ventilator to reduce or remove asynchrony.

Although there are many potential causes of asynchrony, most asynchrony can be managed with simple modifications to the ventilator. At the first sign of asynchrony, the system will detect leaks by, for example, detecting whether inspired volume is different than exhaled volume. Fixing leaks, particularly in NIV, is a crucial first step in improving asynchrony. In NIV, the system will, for example, detect leaks and smoothed waveforms to determine that the face mask is misadjusted and should be fixed. In invasive ventilation, the presence of leaks is similarly detected and results in a recommendation to check that that endotracheal tube (ET-tube) balloon is correctly inflated and that the various fittings and tubings are tightly coupled and not leaking.

When the system detects missed triggers, the sensitivity level (either flow triggering or pressure triggering) of the ventilator would be decreased or recommended to be decreased in an attempt to better detect the missed triggers. Decreasing the sensitivity level can create autotriggering, so the amount of decrease may be incremental and will likely need to trade off the possibility of auto-triggering and double triggering versus missed triggers. The goldilocks position minimizes missed triggers, auto-triggers and double triggers. In some cases, missed triggers are created due to intrinsic peep. This is detected automatically, for example, with the Pes and airway signals as described herein. In other cases, missed triggers are caused by excessive unexhaled volumes during the patient effort, usually created by large inspired volumes or slow exhalation. In this situation, the Pes CDS would recommend lower tidal volumes and faster rates to maintain adequate minute ventilation while minimizing excess volumes retained in the lungs. Using dead space calculations to calculate alveolar ventilation calculation helps maintain adequate "useful" minute ventilation while adjusting respiratory rate and tidal volume. If lowering the tidal volume does not help reduce missed triggers caused by unexhaled volume, bronchodilators or increased PEEP can be implemented or recommended to decrease airway resistance and improve exhalation.

Similarly, double triggering events may trigger the CDS to recommend or automatically increase the ventilator trigger sensitivity or increase the inspiratory time. If the patient effort is continuing beyond the ventilator inspiratory time, a double trigger will occur and disrupt the patient's normal breathing pattern. When in a timed-mode of ventilation, this can be avoided by recommending or implementing an increase in inspiratory time. When the inspiratory time is determined based on indications of patient effort as in pressure controlled ventilation, the inspiratory time can be lengthened by decreasing the ventilator cycling setting, thus alleviating the double triggering. Noise in the waveforms (cardiogenic or otherwise) may also create double triggering, which may be reduced by recommending or implementing an increase in the trigger sensitivity level.

Auto-triggering is often caused by cardiogenic or other noise in the waveforms accidentally triggering a breath when no effort is actually occurring. This can be alleviated by the CDS recommending or automatically increasing the trigger sensitivity. If the CDS is embedded into the ventilator, the cardiogenic or other noise in the waveforms could be filtered more aggressively because of the knowledge that the noise is not associated with effort shown in the Pes.

Similarly, cycling delay and premature cycling can be improved by adjusting the ventilator cycling criteria to better match the patient effort indicated by the Pes signal.

Using these decision support and closed loop approaches, along with others, the Pes CDS could dramatically decrease patient-ventilator asynchrony and improve patient outcomes. A more direct approach, however, would be to simply trigger and cycle with the Pes signal itself. This could be fed back directly to the ventilator control logic to trigger on and cycle off breaths. When the Pes signal is determined to be untrustworthy, the system would switch automatically to airway triggering and cycling like traditionally done.

Intrinsic PEEP Support

During mechanical ventilation complications may be caused by the presence of intrinsic PEEP (PEEPi or autoPEEP), which occurs when exhalation is incomplete and fails to restore the volume of the lung to the function residual capacity. PEEPi, or dynamic hyperinflation, is often noticed by observing a non-zero flow at the end of exhalation; thus an abrupt shift in flow is seen at the onset of inhalation, also referred to as reversal of the flow or flow reversal. PEEPi has been found to occur when the expiratory time is insufficient due to a rapid respiratory rate, an increased resistance, or a compromised compliance. The presence of PEEPi complicates attempts to estimate an appropriate support level for patients. PEEPi is caused by extra unexhaled gas remaining in a patient's lungs at the onset of the next breath, creating an inspiratory threshold load (a positive pressure level above ambient) that the patient's inspiratory muscles must overcome before fresh gas can enter the lungs. Since the inspiratory muscles are displaced from their normal resting position (by hyperinflation) they are mechanically disadvantaged; that is, the direction the respiratory muscles are pulling no longer generates the largest possible change in volume/unit of force. Hyperinflation causes reduced venous return, impaired cardiac function, an increased risk of pulmonary barotrauma, and a reduced respiratory muscle capacity.

PEEPi has detrimental effects on the respiratory system, impeding the patient's ability for efficient ventilation. PEEPi is reported to prolong mechanical ventilation, worsen prognosis, and lead to sleep disruption, alveolar over distention, barotrauma, hypoxemia, decreased venous return, increased right ventricle afterload, and decreased cardiac output. During assisted mechanical ventilation, the threshold load imposed upon the patient by the presence of PEEPi can cause patient-ventilator asynchrony. Patient-ventilator asynchrony is associated with an elevated work of breathing, discomfort, increased sedation, and prolonged mechanical ventilation. The impairments caused by PEEPi can occur in any mechanically ventilated patient, but special precaution should be taken in patients with compromised pulmonary abilities such as patients with COPD.

In the presence of PEEPi, the actual PEEP level may be higher than what the ventilator setting indicates. Having knowledge of the PEEPi levels will enable clinicians to adjust ventilator settings in an effort to reduce or eliminate the presence and effects of PEEPi. The Pes CDS can automatically calculate PEEPi (as discussed elsewhere herein) and recommend or implement conventional measures for improving PEEPi such as increasing expiratory time or decreasing the frequency of mechanical breaths to allow longer expiratory flow towards baseline. However, while these changes may be effective they are not always practical. Similar to the change in the pressure/volume curve, the presence of PEEPi alters a patient's CO2/volume curve. Using an accurate measurement of PEEPi, the Pes CDS can offset PEEPi by gradually increasing external PEEP levels until a more favorable CO2/Volume curve or lower PEEPi measurements are obtained.

PEEPi can be defined as the pressure in the lung at the end of exhalation. One common method to measure the pressure is to impose a pause upon the patient at the end of exhalation. During the pause the pressure will rise to the alveolar pressure, the consequent rise in pressure is the amount of PEEPi. This measurement of PEEPi is referred to as static PEEPi. Another measurement of PEEPi (dynamic PEEPi) is measured by the decrease in Pes from the initiation of a breathe to delivery of flow by the ventilator. This decrease of pressure can be detected with an esophageal sensor.

Using a validated, continuous measurement of Pes, or even spot checked Pes measurements, PEEPi can be determined by waveform analysis. In a ventilated patient, the decrease in Pes caused by the patient breathing effort is marked and tracked until the ventilator either triggers a breath (marked by positive flow) or the airway pressure decreases significantly (typically 1 cm $H_2O$). All patients may have a small amount of PEEPi, but when PEEPi is greater than a certain clinically relevant value (e.g. 5 cm $H_2O$), the CDS will recommend methods of reducing PEEPi to improve patient outcomes. Measurement of Pes will improve the ability of the system to determine the cause of intrinsic PEEP and thus create better decisions on how to reduce the PEEPi. In cases where the inspired tidal volume is large and the respiratory rate is large, a smaller tidal volume or smaller i-time is recommended to allow the patient to exhale more of the inspired tidal volume. In some cases, the patient expiratory resistance or premature airway closure will limit the effectiveness of smaller tidal volumes and i-times. In this case, increased PEEP is recommended to improve patient exhalation, ventilation and outcome. However, excessive PEEP may create high PL values which will increase the likelihood of ventilator induced lung injury (VILI). To avoid this, PEEP should not be increased beyond a threshold of peak Pes or PL calculations (typically around 20 cm $H_2O$). In the case where PL is at its maximum, and reducing Vt and i-time has not improved the condition, the system may suggest bronchodilators or sedation to reduce intrinsic peep.

Pes and airway waveforms also enable more accurate determination of respiratory resistance and compliance. Using Pes and the airway waveforms to calculate resistance and compliance, either through end inspiratory pauses, least squares or other methods known in the field, enables better diagnosis of the causes of intrinsic PEEP. For example, using the waveforms, a dynamic resistance can be estimated using the equation of motion (including effort or Pmus) that allows for better determination of premature airway closure. In this case, the resistance will rise abruptly during the end of exhalation. The pressure at which this increased rise occurs will indicate the PEEP required to overcome the PEEPi caused by premature airway closure. This measurement can then be used to set or recommend a new PEEP level to offset PEEPi. In another example, the system recommends bronchodilators for a patient with high resistance, but recommends a modified breathing pattern for a patient with high compliance.

Passive (sedated or paralyzed) patients may also have intrinsic PEEP driven by a respiratory rate and tidal volume (breathing pattern) that cannot be supported by the recoil pressure generated to exhale. In this case, the intrinsic PEEP is detected by flow reversal at the end of exhalation, where flow does not return to zero before the next inhalation. The system also detects a positive Pes value above baseline indicating retained pressure above baseline trapped in the chest when the next inhalation is forced by the ventilator. The Pes CDS would, in this case, implement or recommend an adjustment of the breathing pattern to maintain adequate alveolar ventilation without imposing intrinsic PEEP. Either decreasing tidal volume, increasing exhalation time, or increasing PEEP would improve PEEPi in passive patients.

PEEP Titration Support

Positive end expiratory pressure, PEEP, is imposed on a patient by a ventilator or valve/device in order to prevent a patient from exhaling all the way to atmospheric pressure. PEEP increases the volume of gas remaining in the lungs at the end of exhalation. PEEP can decrease the shunting of blood through the lungs and improve gas exchange, but also can reduce the stresses on the lungs and especially the alveoli as it keeps them more open and prevents stress/strain from constant closing/collapsing and opening of the alveoli. In normal breathing without a ventilator, the glottis will create slight PEEP that helps keep the lungs from fully collapsing at the end of every breath. Since an endotracheal tube limits the capability of the glottis to create peep, it is generally considered reasonable that all patients on invasive ventilation should have a small amount of PEEP. Sicker patients, for example with lower compliance, may benefit from increased PEEP and the corresponding improvement in oxygenation (and the potential decreases in required fraction of inspired oxygen (FIO2)). However, if PEEP is increased too much, overall pressure and volume in the lung is increased, potentially increasing the potential for barotrauma and volutrauma. As such, PEEP is an important parameter to optimize in most ventilated patients, especially the sicker patients.

A PEEP trial/maneuver is a methodology of slowly increasing PEEP to near excessive levels for two purposes. In sick lungs, often times entire portions of the lungs can collapse and be difficult to open, thus creating much worse gas exchange since only a fraction of the lung is being ventilated. The first purpose of a PEEP maneuver is typically called a recruitment maneuver and the goal is to try to forcefully (without damage) open as much as the lung as possible. The second goal of the PEEP maneuver is to find the optimal amount of PEEP to ensure that the lung does not simply "re-close" after the recruitment maneuver is over. A PEEP maneuver often starts at a baseline PEEP level and increases the PEEP in small steps until a maximum safe PEEP is reached, and then it is slowly decreased back to baseline PEEP. During this procedure, the airway pressure, flow, and volume and oxygenation levels can be monitored and used to determine the compliance at different levels of PEEP. Respiratory compliance often follows an S shape where at the beginning and end small amounts of volume differences can create large pressure differences (FIG. 13). These areas of the compliance curve are to be avoided and may cause lung damage. As such, the Pes CDS endeavors to maintain the normal tidal breathing in the linear portion of the S-shaped lung compliance by setting or recommending PEEP near the bottom of the linear portion and ensuring that the tidal breathing does not exceed the top of the linear portion.

During these maneuvers, it is crucial to protect the lung, so often times the tidal volume will be limited to ensure the peak inspiratory pressure is below 35 cm $H_2O$. Better yet, plateau pressure should be limited, since this is more closely related to the stresses the lung is seeing. The best solution, however, is to limit the PL since this is most closely related to the damaging effects on the lungs. As such, it would be advantageous to monitor Pes during PEEP or recruitment maneuvers. In addition to making sure that the lung is protected by limiting PL during the maneuvers, having dynamic Pes in addition to airway parameters allows for more accurate calculation of respiratory system compliance and resistance and the ability to break down the contributions of different parts of the respiratory system. An embodiment of a PEEP maneuver CDS would include continuous monitoring of PL during the maneuver. When PL approaches the dangerous zone above and below (e.g. maintaining PL between 0 and 10), a warning or indicator can is turned on to prevent further increases or decreases in PEEP. The compliance is computed in real time by tracking the slope of the P-V curve. By tracking the pressure, flow, volume, and Pes waveforms the CDS automatically determines the safe ranges of PEEP during the maneuver as well as calculating the minimum and maximum safe PEEP for the patient as well as the maximum plateau pressure for the patient.

In addition to a PEEP maneuver CDS, a CDS for maintaining safe and effective PEEP titration is envisioned using direct measures of Pes and other airway data. The Pes CDS system monitors PL continuously and makes recommendations or directly modifies PEEP to ensure that PL is maintained between 0 and 10 at end exhalation. In some cases, PL can become negative when compliance is low, potentially injuring the lung and alveoli by allowing it to collapse more than it should. The optimal or recommended value of PEEP that produces a safe PL between 0 and 10 is patient dependent and will be determined by tracking not only that the PEEP is safe, but also its affect on the patient. Using the PaO2/FIO2 ratio or similarly the individual PaO2, FIO2, and/or SpO2 values from the patient, the CDS determines the cost/benefit of increasing PEEP by monitoring the improvement in oxygenation associated with the change. If the CDS does not detect an appropriate increase increases in the oxygenation level (PaO2, SaO2, or SpO2) or oxygenation index (OI or PaO2/FIO2 ratio) after a PEEP change, the system will recommend or automatically implement a decrease or reversal of the PEEP change. The oxygenation index is defined as FiO2 times mean airway pressure divided by PaO2. One embodiment of the PEEP CDS system tracks this index and indicates whether the most recent change in PEEP produced an improved OI. If the OI improved and the PL was still in a safe range (or likely to be in the safe range after an additional change), the system would recommend another increase in PL. If the OI decreased and the PL was still in the safe range (or was in the safe range when the last PEEP change was made), the system would recommend returning to the previous PEEP. Existing data indicates that it is possible to predict the change in PL based on previous changes in PEEP and PL. As such, the system can estimate the maximum safe change in PEEP by estimating how the change in PEEP will affect the PL. The more sick the patient's lung, the more difficult it will be to oxygenate the lung, leading to a higher baseline value of PL (closer to 10). This is particularly useful in ARDS patients who suffer from low to very low compliance and easily collapsed lungs.

Spontaneous Breathing Support

Typically, ventilated patients can be sedated and not breathing or breathing spontaneously. Ventilated spontaneous breathing patients are typically supported by the ventilator to make it easier for the patient to breath, overcoming some of the problems associated with having sick lungs. Spontaneous breathing during ventilation has been shown to improve oxygenation and maintain muscle strength (avoid disuse atrophy of the diaphragm and other respiratory muscles). However, high spontaneous effort can cause fatigue, increase oxygen cost of breathing, cause distress, and can increase PL and the chance of VILI. High spontaneous efforts have been shown to increase local dependent lung stress since the high Ppl during inspiration is predominantly localized in the dependent regions of the lung where it is generated by the diaphragm, leading to volutrauma in the dependent lung. High respiratory drive can also cause increased lung perfusion due to the more negative pressures pulling and retaining vascular blood, which can lead to increased pulmonary edema. Also, high drive can also create asynchrony which can create higher PL through double triggering, missed triggers, and other types of asynchrony.

As such, using Pes to monitor, advise, and/or control the spontaneous breathing effort of the patient can be advantageous to the patient and the clinician (by simplifying the control of the ventilator). Modes of ventilation like pressure support can be adjusted (automatically or after recommendations from the CDS) to optimize patient work of breathing, esophageal pressure time product (PTP), or similar indicators of patient respiratory effort. Standard workloads are between 0.3 J/L and 1.0 J/L per breath or 5-10 J/min. The patient respiratory effort, however, is not the only aspect that needs to be monitored and optimized. Respiratory rate, tidal volume, minute ventilation, ETCO2, saturation, PEEP, plateau pressure, asynchrony, peak PL and other parameters should be monitored and kept in a safe range to optimize the patient breathing pattern and interaction with the ventilator. The Pes data provides a direct measure of the patient effort and critical lung safety parameters such as PL and PEEPi. The Pes CDS can use fuzzy logic, model-based systems, machine intelligence, or similar systems to optimize the interaction between the various important parameters.

In one embodiment, the Pes CDS can be continuously calculating and monitoring patient effort with multiple parameters. At times, work of breathing is the appropriate parameter to track. When there is significant trigger effort (e.g. during PEEPi) or effort beyond the inspiration, the pressure time product (PTP) may be a better indicator of actual patient effort. By monitoring the effort outside of inspiratory flow periods, the Pes CDS can determine when to change or recommend new modes of ventilation or to optimize the current ventilator settings using WOB or PTP. In general, different parameters for patient effort or lung protection may be used at different times or for different patients based on current conditions or patient demographics or diseases.

The Pes CDS can suggest changes in many ventilator settings including: PSV level, PCV level, PCV i-time, trigger sensitivity, cycle sensitivity, SIMV rate, guaranteed volume, and many other parameters. However, the Pes CDS may also recommend non-ventilator related therapies such as sedation. In some patients with large effort and sick lungs, the system will recommend to increase patient sedation rather than potentially damage the lungs by continually increasing support. Similarly, bronchodilator therapy is suggested if the patient is struggling with high resistance or poor exhalation.

In one embodiment, the Pes CDS could adjust the ventilator to maintain muscle pressure between 5 and 10 cm $H_2O$ (or maintain the respiratory effort in an acceptable or normal range) while ensuring that PL remains below a lung safety limit such as 20-25 cm $H_2O$. If the effort cannot be maintained without exceeding the safe PL, then sedation or other non-ventilator strategies would be suggested. If sedation is implemented, the system could then provide support for non-spontaneous breathing by ensuring that the breathing pattern is safe and maintains low PL and provides adequate alveolar minute ventilation to maintain safe $CO_2$ and oxygen levels. $ETCO_2$ and saturation monitoring, when available, is also useful to the CDS to estimate parameters frequently found in blood gases or derived from blood gases, but using blood gas data is more accurate but less continuous and more costly.

In another embodiment, the Pes CDS would constantly monitor patient oxygen cost of breathing, by estimating patient effort. Patient effort is directly related to oxygen cost of breathing. PTP of the diaphragm, which can be estimated with Pes, is known to correlate well with oxygen cost of breathing. In particularly sick patients, it may be beneficial for the patient to not expend significant energy in breathing when that energy could be put to better use healing other aspects of the body. As such, the Pes CDS could display and monitor estimated oxygen cost of breathing and provide decision support or closed loop control to maintain oxygen cost of breathing in an acceptable range.

In another embodiment, both Pes and Pga is measured and monitored simultaneously. Similar to the methods of determining reliability, proper placement, and proper inflation of the Pes sensor, the Pga sensor can be monitored and reliability determined. By subtracting Pga from Pes, the pressure generated by the diaphragm (Pdi) is calculated directly and represents the contribution to the work of breathing done by the diaphragm. Pdi is utilized for multiple purposes to improve patient ventilator interaction. First, high values of Pdi during exhalation indicate forced exhalation. When high Pdi is determined during exhalation (higher than baseline at end exhalation and early in the initiation of a breath), the system would indicate forced exhalation and provide feedback on how to correct this situation, including bronchodilator treatment, sedation, higher PEEP, lower tidal volume, or generally decreased ventilatory support. Another use of Pdi that has not been disclosed previously is determining patient comfort or patient tolerance for the current work of breathing. In normal tidal breathing, the diaphragm does the majority of the work in inhaling. When the lung is sick or the diaphragm is weak, the diaphragm cannot always do all the work necessary to achieve the appropriate tidal volume and other inspiratory muscles (accessory muscles) must be used to breath. In this embodiment, the Pes CDS determines the relative ratio of Pdi to Pmus or WOB, the fraction of work done by the diaphragm. When the fraction of work done by the diaphragm exceeds a threshold value or gradually decreases over time, the patient is no longer able to maintain the required effort to breath with only the diaphragm and the system recommends or implements an increase in support, or perhaps sedation or BD treatment. As discussed above, the increase in support can be done safely by maintaining PL in a safe range (0 to +10 cm $H_2O$), maintaining low tidal volume (<6 or 8 ml/kg of ideal body weight), maintaining low plateau pressure, maintaining low driving pressure, and maintaining adequate work of breathing.

Lung Protection Support

Lung protective strategies are an important aspect of patient ventilation. Ventilator Induced Lung Injury (VILI) is a term that covers many different types of potential lung injury including barotrauma (lung injury caused by high pressures), volutrauma (lung injury caused by high volume, stretching), and other injuries such as alveolar damage caused by the opening and closing of alveoli. Traditionally, VILI is avoided by limiting tidal volumes to 4-8 mls per kg of ideal body weight (calculated based on patient height, since being under/overweight does not normally change the size of the lungs) and minimizing plateau pressure (Pplat) or peak inspiratory pressure (PIP). Pplat is more accurate than PIP since Pplat estimates the pressure inside the lungs by subtracting the pressure due to resistance in the airways. PIP can be deceptively high in patients with highly resistive airways. More recently researchers have found that transpulmonary pressure may be the most effective measure in trying to avoid VILI. The fraction of driving pressure used to overcome lung and chest wall elastance does not contribute to PL and does not contribute to damage creating pressure. However, lung and chest wall elastance vary both intrapatient (intra-hospital stay) and interpatient. Therefore, indirectly measuring PL by subtracting an estimate of lung and chest wall elastance is difficult and a direct measure of PL is necessary to accurately estimate PL, the true lung distending pressure that may cause VILI. In addition to this complexity, PL varies across the lung and is typically higher in the dependent regions (lower) of the lung, particularly with respiratory effort. Atelectasis also predominates in the lower portion of the lung, further complicating accurate calculation of the damage that may be caused in different lung compartments.

In a preferred embodiment, lung protection is managed by directly measuring PL using esophageal pressure. PL can then be used to manage and limit patient ventilation to protect the lungs. Instead of (or in addition to) limiting plateau pressure or PIP, the Pes CDS provides feedback, recommendations, alarms, warnings or closed loop control to ensure that the PL never exceeds the safe limit (typically 20-25 cm $H_2O$). The Pes CDS provides advice or closed loop control of pressure support/control levels, maximum tidal volume, inspiratory time, PEEP, or other parameters to maintain lung protection. As discussed above, however, other patient priorities exist as well. For example, the patient must be adequately oxygenated and ventilated, so a minimum minute ventilation must be maintained. The system can optimize the breathing pattern by adjusting the tidal volume, respiratory rate, delivery flow, delivery flow pattern, pressure control level, and other ventilator settings in order to provide adequate ventilation in a safe and effective manner. For example, if the respiratory rate is low (say 10 bpm) and the tidal volume is high (say 8 mls/kg) producing a high PL that may induce VILI (25 cm $H_2O$), the system could recommend or automatically change the ventilator settings to increase the respiratory rate and decrease the tidal volumes. When the patient is not breathing spontaneously, this can be done by simply adjusting the tidal volume, pressure control, i-time, e-time, respiratory rate, and other similar parameters on the ventilator. When the patient is breathing spontaneously, the spontaneous tidal volume and respiratory rate are at least partially driven by the patient. As such, adjusting tidal volume, peak pressures, and respiratory rate may be a more complicated relationship between the patient and ventilator settings. As such, the system will closely track the patient response to ventilator changes and iteratively improve the settings to reach the optimal setup. In some cases, the ventilator alone may not be able to reach an acceptable status quo. In this case, other non-ventilator settings recommendations are suggested including sedation, bronchodilators, cleaning or unkinking the ET-Tube, reducing the leak (adjusting ET-Tube balloon, adjusting the face mask), etc. In other cases, the Pes CDS may recommend ECMO to improve patient oxygenation without harming the lung.

Patient models can be used to estimate the effect of each parameter change on the overall "patient system" to recommend the best possible combination of settings. This can be done in mechanically or spontaneously breathing patients. The model would, for example, use airway parameters (volume, pressure, flow, CO2), saturation, Pes, patient demographic data, drug data (what drugs the patient is currently on, sedation level, bronchodilators, etc.) and/or diagnosis data (COPD, ARDS, asthma, etc.) to create a good model. The model is preferably trained dynamically with patient data so as to track the patient condition throughout the patients stay and closely track both worsening and improving conditions.

In one embodiment, when the Pes pressure is trusted and working well, the ventilator could use PL in a closed loop system to dynamically adjust pressure both inter and intrabreath. Thus, instead of using airway pressure to control flow and pressure supplied to the patient, Pes is used to control the ventilator. This is more than just adjusting the airway pressure control limits common to pressure supported breathing, this involves directly using PL to control the flow/pressure generator in the ventilator. As a backup for when the Pes pressure may become less reliable, the airway pressure parameters are used to control the airway flow and/or pressure when Pes can no longer be trusted, whether in short durations or long durations if more severe problems hamper Pes sensor use. In this embodiment, the control algorithm is similar to common modes of ventilation like PAV or PSV but instead of using Paw to control the ventilator valves, it uses PL. The system would present a recommended safe range of PL and allow the clinician to either select a fraction of PL to use to ventilate the patient, or to select a maximum PL. In one embodiment, similar to the pressure regulated volume control ventilation, the system would provide flow such that the PL never exceeded a clinician set threshold while delivering a clinician set tidal volume. The control algorithm adjusts the flow and i-time to both maintain low PL and deliver sufficient volume, much like the PRVC ventilation. Like NAVA, which uses diaphragm activity to trigger the breath only, a PL controlled ventilator mode dramatically increases synchrony by triggering on the first signs of effort rather than Paw which may not show effort for some time, in particular because of PEEPi. Unlike NAVA, a PL controlled ventilator mode would be able to deliver maximum tidal volume safely, which is particularly difficult in extremely sick patients.

In one embodiment, PL can be calculated in two different methods and used to limit pressure and flow delivered to the patient. Pes can be directly used to calculate PL or Paw*Ecw/Ers can be used to calculate PL (using Pes airway parameters to calculate Ecw and Ers). Although theoretically these values may be the same, in reality they can vary. As such, in one embodiment, both values of PL can be continuously calculated and the most trustworthy one can be utilized. This can be calculated based on patient diagnosis, patient position, inspiratory drive, breathing pattern and/or patient demographics or from waveform data. In another embodiment, both can be tracked and using abundance of caution, the largest one is used for advice or control to protect the lung.

Bronchodilator and Sedation Support

Use of Pes and PL can also improve the use of bronchodilators and sedation. Constant monitoring of Pes can provide better estimates of resistance, compliance, and other physiologic parameters. Using Pes in the equation of motion Paw=R*f+V/C+PEEP+Pes can remove the need for breathing interruptions like end inspiratory pauses to accurately calculate resistance and compliance in real time. When resistance is high, bronchodilators can be recommended. When bronchodilators are started or changed, resistance can be monitored to see improvements in physiology of the patient (decreases in resistance, etc.). Increasing Pes during exhalation indicates forced exhalation which may be another indication of the need for adding or increasing bronchodilators or other techniques to improve patient breathing. Because accurate measurements of resistance can often not be made from airway sensors, bronchodilators are used routinely, even on patients who may not need them. Accurate measurements of resistance can determine who needs BD treatment and who doesn't. It can also indicate whether BD treatment is effective, by measuring the change in resistance before and after BD treatment.

In one embodiment, the Pes CDS monitors airway and Pes waveforms and calculates an accurate estimate of respiratory system resistance. If the resistance reaches a threshold value determined by the patient diagnosis, patient position, size of the ET-TUBE, and/or generally accepted practice, then the system recommends BD treatment. After initiation of BD treatment, the system tracks the resistance and if there is not a significant improvement in resistance or decrease in PL, then the BD treatment would be discontinued or a recommendation to discontinue BD would be suggested. In another embodiment, the pressure from the ET-Tube cuff would be used to estimate tracheal pressure, as described previously. In this case, the resistance of the ET-Tube is separated from the respiratory system resistance. The ET-Tube resistance is Ptracheal−Paw/flow and the physiologic resistance is Pes or PL−Ptracheal/flow. If the high respiratory system resistance is due to a high resistance of the ET-Tube, BD treatment will not be successful in significantly reducing system resistance. In this case, the system recommends suctioning, replacing, or unkinking the ET-Tube rather than BD treatment. When physiologic resistance is available, it is the preferred method of determining when BD treatment would be successful, using a physiologic threshold like described above.

Detecting Physiologic Changes

As discussed previously, continuous monitoring of Pes can provide important physiologic information that can help determine lung and patient physiologic changes. In an embodiment, the Pes CDS monitors Pes and/or other parameters such as but not limited to airway pressure, flow, and volume. In the system, the Pes and airway parameters are used to calculate accurate estimates of patient physiologic parameters such as lung and/or respiratory system compliance and resistance, time constant, and changes in these parameters over time—both inter and intra-breath. This data is then used to detect when physiology is changing in a clinically relevant manner. As already discussed above, increases in resistance can indicate problems with the respiratory system or problems with the ventilator ET-Tube. Changes in resistance that occur at end-exhalation can indicate premature airway closure and increased PEEP would be recommended. Rapid onset of decreased compliance could indicate lung collapse and would generate a warning or alarm. Symptoms of ARDS and COPD, two of the most common respiratory diseases, could be automatically detected with the help of Pes and an alert can be provided to the clinician.

Examples above indicate the use of the Pes CDS system as a smart alarm system which doesn't just indicate low level problems like high pressures, but also indicates high level problems like lung disease progression, pneumothorax, and other problems that are much more clinically relevant to the physician or therapist.

Spot Checking with Pes

In many cases, clinicians choose to not continuously monitor Pes but instead only use Pes sensors to spot check a patient, or in some cases only difficult or struggling patients. In this case the Pes CDS still provides important information to the clinician. The Pes CDS would be used continuously, even during the times that the Pes sensor is not in place. When it is time for a spot check, the Pes CDS can help initiate Pes sensor placement and ensure accurate measurements as described previously. In addition, patient data can be monitored and trended such that the Pes CDS will determine when settings or patient response to settings is different enough that a new Pes spot check should be done. In stable patients where the settings and responses are not changing significantly, a new spot check is unlikely to be needed. The Pes CDS can reduce the unnecessary use of Pes sensors for spot checking while increasing use when the spot check is likely to provide useful information. In a preferred embodiment, the Pes CDS would create a model of the patient physiology including resistance, compliance, and flow, pressure and volume waveforms and monitor these parameters and the ventilator settings to determine when the patient or settings have changed significantly enough to require a new spot check. For example, ventilator mode changes, patient alertness, agitation, sedation level or RASS score changes, or large resistance or compliance changes would result in the CDS suggesting it is time for a new spot check.

Non-Limiting Examples

The description of the present application has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A system to improve operation of a ventilator comprising:
   two or more sensors to provide measurement data for each of esophageal pressure data, airway pressure data, and airway flow data from a patient being ventilated;
   a processor electronically coupled to the sensors and receiving the measurement data therefrom, the processor continuously compares the esophageal pressure data with changes to both the airway pressure data and the air flow data to determine an accuracy of the esophageal pressure data; and displaying, on a display, an automatic accuracy indicator to indicate a reliability of the esophageal pressure data.

2. The system of claim 1, wherein the accuracy of the esophageal pressure data is determined by automatically comparing the airway pressure data to the esophageal pressure data during one or more of a trigger portion of a breath, an end exhalation portion of a breath, or an end inspiratory pause of a breath from the patient being ventilated.

3. The system of claim 2, wherein the automatically comparing occurs over multiple breaths from the patient being ventilated and the processor further determines a trend that is included in the accuracy of the esophageal pressure data.

4. The system of claim 1,
wherein the display indicates a status that is used as part of a clinical decision support (C.D.S.) to improve the use of the ventilator, the status includes one or more of a warning, an automatic color coding of an esophageal waveform to indicate
that an accuracy of the esophageal pressure data is either reliable or unreliable, and
one or more parameters derived from the esophageal waveform.

5. The system of claim 4, wherein the status on the display is used to improve one or more of a placement and setup of the two or more sensors to provide the esophageal pressure data.

6. The system of claim 4, wherein the processor automatically determines whether an occlusion test is successful from an analysis of a change in esophageal pressure divided by the change in airway pressure during times of zero flow.

7. The system of claim 6, wherein the system uses one or more of the esophageal pressure data, the airway pressure data and the airway flow data to indicate a direction to relocate the two or more sensors in an esophagus of the patient.

8. The system of claim 1, wherein the processor uses the esophageal pressure data to determine an intrinsic PEEP in the patient.

9. The system of claim 8, wherein the intrinsic PEEP is automatically detected by measuring a change in esophageal pressure data during a patient triggering before a change to one or more of the airway pressure data and the airway flow data at a start of a breath of the patient.

10. The system of claim 8, wherein the processor uses settings from a ventilator control algorithm as input along with a degree of the intrinsic PEEP to automatically calculate changes to settings in the ventilator.

11. The system of claim 10, wherein the settings in the ventilator include one or more of a PEEP setting, a sensitivity level, a cycling criteria, a pressure support level, a tidal volume, a breath rate, and an inspiration-expiration (I:E) ratio.

12. The system of claim 1, wherein the processor uses a transpulmonary pressure data to calculate a change in a PEEP.

13. The system of claim 12, wherein the PEEP is managed by maintaining the transpulmonary pressure data at end of exhalation of the patient in a predetermined range.

14. The system of claim 13, wherein the processor uses one or more of a patient diagnosis, patient lung characteristics, and ventilator settings to calculate a change in the PEEP.

15. The system of claim 14, wherein the transpulmonary pressure data is used by the processor to calculate a change in a tidal volume of the patient to maintain peak transpulmonary pressure below a predetermined level.

16. The system of claim 1, wherein the processor automatically make changes to a ventilator control algorithm when the accuracy of the esophageal pressure data is above a threshold of accuracy.

17. The system of claim 16, wherein the processor automatically make changes to a ventilator control algorithm including using the esophageal pressure data to control breath delivery.

18. The system of claim 1, further comprising;
based on the change in the esophageal pressure data during spontaneous breathing, automatically displaying on the display, positional information for repositioning one of the two or more sensors for measuring the esophageal pressure data relative to a stomach of the patient.

19. A method to improve operation of a ventilator comprising:
accessing measurement data, by a computer processor, from two or more sensors for each of esophageal pressure data, airway pressure data, and airway flow data from a patient being ventilated;
continuously comparing, by the computer processor, the esophageal pressure data with changes to each of the airway pressure data and the air flow data to determine an accuracy of the esophageal pressure data; and
displaying, on a display, an automatic accuracy indicator to indicate a reliability of the esophageal pressure data.

20. A computer program product for improving operation of a ventilator comprising a computer readable storage medium having a computer readable program stored therein, wherein the computer readable program, when executed on a computing device, causes the computing device to perform:
accessing measurement data from two or more sensors for each of esophageal pressure data, airway pressure data, and airway flow data from a patient being ventilated;
continuously comparing the esophageal pressure data with changes to each of the airway pressure data and the air flow data to determine an accuracy of the esophageal pressure data; and
displaying, on a display, an automatic accuracy indicator to indicate a reliability of the esophageal pressure data.

* * * * *